United States Patent
Plebanski et al.

(10) Patent No.: US 11,573,234 B2
(45) Date of Patent: Feb. 7, 2023

(54) PREDICTING RESPONDERS TO CYCLOPHOSPHAMIDE THERAPY

(71) Applicant: Royal Melbourne Institute of Technology, Melbourne (AU)

(72) Inventors: Magdalena Plebanski, Melbourne (AU); Mutsa Tatenda Madondo, Darlinghurst (AU)

(73) Assignee: ROYAL MELBOURNE INSTITUTE OF TECHNOLOGY, Melbourne (AU)

( * ) Notice: Subject to any disclaimer, the term of this patent is extended or adjusted under 35 U.S.C. 154(b) by 272 days.

(21) Appl. No.: 16/614,883

(22) PCT Filed: May 18, 2018

(86) PCT No.: PCT/AU2018/050478
§ 371 (c)(1),
(2) Date: Nov. 19, 2019

(87) PCT Pub. No.: WO2018/209404
PCT Pub. Date: Nov. 22, 2018

(65) Prior Publication Data
US 2020/0158733 A1    May 21, 2020

(30) Foreign Application Priority Data
May 19, 2017   (AU) ................. 2017901908

(51) Int. Cl.
*G01N 33/53* (2006.01)
*G01N 33/574* (2006.01)
*C07K 16/28* (2006.01)
*G01N 33/50* (2006.01)
*A61K 31/675* (2006.01)

(52) U.S. Cl.
CPC ... *G01N 33/57484* (2013.01); *C07K 16/2866* (2013.01); *G01N 33/5011* (2013.01); *A61K 31/675* (2013.01); *G01N 2333/7158* (2013.01)

(58) Field of Classification Search
CPC combination set(s) only.
See application file for complete search history.

(56) References Cited

U.S. PATENT DOCUMENTS

2007/0031896 A1   2/2007 Wu et al.
2009/0208975 A1   8/2009 D'Costa et al.

FOREIGN PATENT DOCUMENTS

| JP | 2015526709 A | 9/2015 |
| WO | 2009042215 A2 | 4/2009 |
| WO | 2014005909 A1 | 1/2014 |
| WO | 2014125041 A1 | 8/2014 |

OTHER PUBLICATIONS

Zhao et al, J Immunol, 188:6055-6062, 2012.*
Australian Patent Office, International Search Report and Written Opinion for PCTAU2018/050478, dated May 19, 2017, 17 pages.
Foucher Ed, et al, "IL-34- and M-CSF-induced mascrophages switch memory T cells into Th17 cells via membrane IL-1a", European Journal of Immunology, 2015, 46(4):10291102. doi: 10.1002/eji.201444606.
Karni, A. et al., "Cyclophosphamide modulates CD4+ T cells into a T helper type 2 phenotype and reverses increased IFN-gamma production of CD8+ T cells in secondary progressive multiple sclerosis", Journal of Neuroimmunology, 2004, 146(1-2): 189-198.
Madondo MT et al, "Low dose cyclophosphamide: Mechanisms of T cell modulation", Cancer Treatment Reviews, 2016, 42:3-9. doi: 10.1016/j.ctrv.2015.11.005.
Oelkrug C. et al., "Enhancement of T cell recruitment and infiltration into tumours", Climnical and Experimental Immunology, 2014, 178(1):1-8. doi: 10.1111/cei.12382.
Zsiros E. et al., "The Ovarian Cancer Chemokine Landscape is Conducive to Homing of Vaccine-Primed and CD3/CD28-Constimulated T Cells Prepared for Adoptive Thereapy", Clinical Cancer Research, 2015, 21(12:2840-2850, doi: 10.1158/1078-0432.CCR-14-2777.
Bettelli, Estelle et al. Reciprocal developmental pathways for the generation of pathogenic effector Th17 and regulatory T cells, vol. 441/May 11, 2006, Nature, 4 pages.
Brodsky et al. Intensive immunosuppression with high dose cyclophosphamide but without stem cell rescue for severe autoimmunity: Advantages and disadvantages, Autoimmunity, 2008, 41(8) 596-600.
Cronshaw, Darran G. et al. Activation of Phosphoinoside 3-Kinases by the CCCR4 Ligand Macrophage derived chemokine is a dispensable signal for T Lymphocyte chemotaxis; Journal of Immunology 2004: 172:7761-7770.
Gooden, MJM et al. The prognostic influence of tumour-infiltrating lymphocytes in cancer: a systematic review with meta-analysis, Bristish Journal of Cancer (2011) 105, 93-103.
Kishimoto, Chiharu et al. Immunosuppression with high doses of cyclophosphamide reduces the severity of myocarditis bus increases the mortality in murine coxsackievirus B3 myocarditis, Cyclophosphamide in Coxsackievirus B3 Myocarditis, pp. 982-989.
Kondo, Takaaki et al. Human memory CCR4+ CD8+ T cell subset has the ability to produce multiple cytokines, The Japanese Society for Immunology vol. 21, No. 5, pp. 523-553 2009.
Kovacsovics-Bankowski Magdalena et al. Detailed characterization of tumor infiltrating lymphocytes in two distinct human solid malignancies show phenotypic similarities, Journal for ImmunoTherapy of Cancer, 2014, 2:38, 12 pages.
Lavareille, Aurore de et al. Clonal Th2 cells associated with chronic hypereosinophilia: TARC-induced CCR4 down-regulation in vivo, Eur. J. Immunol. 2001 31: 1037-1046.
Liu, Pu et al. Administration of cyclophosphamide changes the immune profile of tumor-bearing mice, J Immunother. Jan. 2010; 33(1): 53-59.

(Continued)

*Primary Examiner* — Mark Halvorson
(74) *Attorney, Agent, or Firm* — Storella & Witt, LLP

(57) ABSTRACT

The present disclosure is based on detecting CC chemokine receptor 4 (CCR4) expression on T effector cells to diagnostically or prophylactically predict subjects, in particular those with a gynaecological cancer who will respond to treatment with low dose cyclophosphamide.

21 Claims, 15 Drawing Sheets
Specification includes a Sequence Listing.

(56) References Cited

OTHER PUBLICATIONS

Lutsiak M.E., et al. Inhibition of CD4+25+ T regulatory cell function implicated in enhanced immune response by low-dose cyclophosphamide, Immunobiology, Blood, Apr. 2005, vol. 10:7.
Mariani, Margherita, Dominance of CCL22 over CCL17 in induction of chemokine receptor CCR4 desensitization and internalization on human Th2 cells, Eur. J. Immunol 2004. 34:231-240.
Notice of Reasons for Rejection for Japanese Patent Application No. 2020-514307, (Translation) dated Mar. 31, 2022, 5 pages.
Zon, 4 Cyclophosphamide Analogues, Progress in Medicinal Chemistry, vol. 19, Edited by G. P. Ellis and G.B. West, Elsevier Biomedical Press—1982, 42 pages.

\* cited by examiner

MNPTDIADTT LDESIYSNYY LYESIPKPCT KEGIKAFGEL FLPPLYSLVF

VFGLLGNSVV VLVLFKYKRL RSMTDVYLLN LAISDLLFVF SLPFWGYYAA

DQWVFGLGLC KMISWMYLVG FYSGIFFVML MSIDRYLAIV HAVFSLRART

LTYGVITSLA TWSVAVFASL PGFLFSTCYT ERNHTYCKTK YSLNSTTWKV

LSSLEINILG LVIPLGIMLF CYSMIIRTLQ HCKNEKKNKA VKMIFAVVVL

FLGFWTPYNI VLFLETLVEL EVLQDCTFER YLDYAIQATE TLAFVHCCLN

PIIYFFLGEK FRKYILQLFK TCRGLFVLCQ YCGLLQIYSA DTPSSSYTQS

TMDHDLHDAL (SEQ ID NO:1)

FIGURE 1

SEQUENCE LISTING

<160> NUMBER OF SEQ ID NOS: 1

<210> SEQ ID NO 1
<211> LENGTH: 360
<212> TYPE: PRT

<213> ORGANISM: Homo sapiens

<400> SEQUENCE: 1

```
Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
            20                  25                  30

Gly Ile Lys Ala Phe Gly Glu Leu Phe Leu Pro Pro Leu Tyr Ser Leu
        35                  40                  45

Val Phe Val Phe Gly Leu Leu Gly Asn Ser Val Val Val Leu Val Leu
    50                  55                  60

Phe Lys Tyr Lys Arg Leu Arg Ser Met Thr Asp Val Tyr Leu Leu Asn
65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
                100                 105                 110

Ile Ser Trp Met Tyr Leu Val Gly Phe Tyr Ser Gly Ile Phe Phe Val
            115                 120                 125

Met Leu Met Ser Ile Asp Arg Tyr Leu Ala Ile Val His Ala Val Phe
    130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
        195                 200                 205

Leu Gly Leu Val Ile Pro Leu Gly Ile Met Leu Phe Cys Tyr Ser Met
    210                 215                 220

Ile Ile Arg Thr Leu Gln His Cys Lys Asn Glu Lys Lys Asn Lys Ala
225                 230                 235                 240

Val Lys Met Ile Phe Ala Val Val Val Leu Phe Leu Gly Phe Trp Thr
                245                 250                 255

Pro Tyr Asn Ile Val Leu Phe Leu Glu Thr Leu Val Glu Leu Glu Val
            260                 265                 270

Leu Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
            340                 345                 350

Asp His Asp Leu His Asp Ala Leu
        355                 360
```

PREDICTING RESPONDERS TO CYCLOPHOSPHAMIDE THERAPY

All documents cited or referenced herein, and all documents cited or referenced in herein cited documents, together with any manufacturer's instructions, descriptions, product specifications, and product sheets for any products mentioned herein or in any document incorporated by reference herein, are hereby incorporated herein by reference in their entirety.

This application claims priority from Australian application no. AU2017901908 filed 19 May 2017. The entire contents of this application are incorporated by reference herein.

FIELD OF THE DISCLOSURE

The present disclosure is based on detecting CC chemokine receptor 4 (CCR4) expression on T effector cells to diagnostically or prophylactically predict subjects, in particular those with a gynaecological cancer who will respond to treatment with low dose cyclophosphamide.

BACKGROUND

Gynaecological cancers are cancers of the female reproductive tract and include, cervical, vaginal, vulva, uterine, and ovarian cancers. Globally, these cancers account for more than 15% of all cancer incidences in women with over 1 million cases diagnosed annually (Bray F et al., (2013) 1; 132(5):1133-45). The annual mortality rate is just under 500,000, contributing to 14% of all reported cancer related deaths in women. Uterine, cervical and ovarian cancers are the most prevalent of gynaecological cancers, while vaginal and vulva cancers are rare and contribute to less than 0.6% of the annual cancer incidence in women.

Prevalence patterns in Australia differ from global trends, which are driven by a high prevalence of cervical cancer in developing countries. On average, 12 Australian women are diagnosed with gynaecological cancers daily, giving a total annual incidence of over 4,500 cases and contributing to just under 10% of all reported cancer cases in women (Report to the nation-gynaecological cancer 2012. In: Australia C, editor. Surry Hills, NSW2012). Uterine and ovarian cancers are of greatest public health concern in Australia because uterine cancers are the most prevalent, accounting for 44% of gynaecological cancer cases. While ovarian cancers account for 28% of cases, they contribute to over half of the deaths due to gynaecological cancers.

Premature deaths caused by gynaecological cancers have a negative effect on the economy. Gynaecological cancers accounted for over 8% of all burden of disease due to cancer in women, with over 22,000 disability-adjusted life years (DALY) in 2012. Within the 2004-2005 financial year, gynaecological cancer hospitalisations cost the nation AU$63 million, with majority of the money spent on ovarian (AU$25 million), uterine (AU$22 million) and cervical (AU$11 million) cancers.

The majority of ovarian and uterine cancers occur due to sporadic somatic mutations, while 5% of ovarian cancers and 10% of uterine cancers have a hereditary basis (Whang J D et al., (1997) October; 12(5):383-9)). The role of specific genetic mutations in tumourigenesis is still largely unclear, however there are several genetic aberrations in tumour suppressor genes and oncogenes that have been commonly associated with the onset of disease. The most common somatic mutation that gives rise to sporadic ovarian cancer is in the p53 gene. Mutations in p53 are also frequently seen in uterine cancers.

Ovarian cancer (OC) is the fifth most common cause of cancer death in women. More than half of these women currently die within five years of diagnosis (Luvero D et al., (2014) Therapeutic Advances in Medical Oncology 6:229-239). There are several forms of ovarian cancer which include epithelial cancer, germ-line cancer of the ovaries and ovarian stromal cancer. Epithelial ovarian cancer represents the most common form of the disease.

Ovarian cancer is a disease that primarily affects post-menopausal women with the median age for diagnosis at 63 years of age. However, the disease can affect women of all age groups.

The classification of ovarian cancer stage is based upon the extent of localisation versus spread of the disease beyond the ovaries. Stage 1 ovarian cancer is confined to one or both of the ovaries. Stage 2 disease involves a tumour in one or both ovaries with pelvic extension. Stage 3 disease involves a tumour in one or both ovaries with microscopically confirmed peritoneal metastasis outside the pelvis and/or regional lymph node metastasis. Stage 4 ovarian cancer is characterised by distant metastasis beyond the peritoneal cavity. Ovarian cancers tend to be diagnosed at advanced stages and this is due to the topographical location of the primary lesion. Symptoms only manifest once the tumours have developed enough to cause physical discomfort. Even then, the symptoms (which include abdominal or pelvic pain, frequent urination and vomiting) are vague and can often be mistaken for other disease such as gastritis, irritable bowel syndrome or urinary infections. In contrast, uterine cancers are diagnosed earlier on as a result of abnormal vaginal bleeding often seen in presenting patients. Upon presentation, patients are diagnosed via histological analysis of tissue biopsies and the disease is staged based on the extent of spread and organ involvement.

Ovarian cancer spreads via local shedding from the ovarian epithelium into the peritoneal cavity followed by implantation on the peritoneum and local invasion of the bowel and bladder. The presence of lymph node involvement in ovarian cancer is evident in all stages of diagnosed ovarian cancer.

The survival of patients with ovarian cancer is a function of the stage at which the disease is diagnosed, with 5 year survival decreasing with advanced disease.

Ovarian cancer is often detected with the presentation of overt clinical symptoms, most notably the presentation of abdominal pain, an adnexal mass, abdominal bloating and urinary urgency. Detection of ovarian cancer at an early stage (i.e. stage 1) results in approximately 90% cure rate using standard surgery and chemotherapy.

Current screening methods to detect ovarian cancer at an early stage are insufficient. The current practice for ovarian cancer screening employs the use of CA125 and transvaginal ultrasound (sonography). Rising serum levels of CA125 are associated with ovarian cancer and subsequent utilisation of transvaginal ultrasounds helps detect the presence of ovarian cancer. Confirmation of ovarian disease is based upon invasive procedures such as laparotomy. However the use of CA125 is ineffective for general population screening due to issues of limited sensitivity, limited specificity and a poor positive predictive value of <3% (Bast (2003) J. Clin Oncol. 21(10 Suppl):200-205).

First line treatment of gynaecological cancers such as ovarian cancer involve debulking surgery to remove all macroscopic disease leaving less than 2 cm of residual disease. The surgery may involve laproscopic or total hysterectomy, bilateral salpingo-oophorectomy and lymphadenectomy based on the spread of disease. Depending on the stage of the disease, following surgery, adjuvant radiotherapy or chemotherapy with carboplatin and epirubicin for uterine cancer patients or carboplatin and paclitaxel for ovarian cancer, may also be recommended. In some cases patients are unfit for surgery due to the presence of medical comorbidities or the extent of disease spread. These patients undergo primary radiotherapy for uterine cancer or chemotherapy for ovarian cancer.

While primary treatment of gynaecological cancers is relatively successful, disease recurrence often occurs. Second line therapy for recurrent disease consists of radiotherapy, hormone therapy or chemotherapy. The standard chemotherapy for uterine and ovarian cancers consists of platinum based cisplatin and carboplatin respectively and response rates hover around 20% (Fung-Kee-Fung M et al., (2007) Current oncology October; 14(5):195-208). Subsequent treatment options for patients with recurrent disease are based on the classification of disease. If disease recurrence occurs less than 6 months following the last cycle of platinum based treatment, the disease is deemed platinum resistant while platinum sensitive disease recurs more than 6 months following treatment. For treatment of platinum resistant disease, alternative chemotherapy strategies including treatment with texanes (doxetaxel and paclitaxel), anthracyclines (doxorubicin and liposomal doxorubicin), oxazaphosphorines (cyclophosphamide and ifosfamide), gemcitabine, etopiside and topotecan are used, each have relatively comparable response rates of between 12-30% (Handolias D et al., (2013) Asia-Pacific journal of clinical oncology 2013 May 29).

There are two types of criteria used to assess patient response to treatment, the response evaluation criteria in solid tumours (RECIST) or the gynaecological cancer intergroup (GCIG) CA125 response criteria. The RECIST criteria uses computed tomography (CT) or magnetic resonance imaging (MRI) to measure the largest diameter of the targeted tumour or any de-novo appearance of new lesions and the GCIC measures serum levels of CA125. Using a combination of both criteria, patient responses can be categorised into complete response (CR), partial response (PR), stable disease (SD) ad progressive disease (PD) (Rustin G J et al., (2011) International journal of gynaecological cancer society February; 21(2):419-23).

Low dose cyclophosphamide is often used to treat advanced stage and/or recurrent cancers such as recurrent ovarian cancer (Handolias et al. (2013) Asia Pac J Clin Oncol 12(1): e154-e160). However, low dose cyclophosphamide results in clinical benefit for only 25-44% of women with recurrent ovarian cancer (Liu et al. (2010) J Immunother 33:53-59; Ghiringhelli et al. (2007) Cancer Immunol Immunother 56(5):641-8). It is currently not known who will respond to which drug, and by the time it is realized that a particular drug is not working, further treatment may be ineffective. Therefore, it would be beneficial to be able to predict subjects that will respond to treatment with low dose cyclophosphamide, either before therapy begins, or within the first cycle of treatment. This would allow low dose cyclophosphamide to be given to subjects that will respond to treatment earlier in the treatment regime and subjects predicted not to respond to treatment to be moved on to other treatment protocols.

Accordingly, there is a need in the art for methods that can predict subjects that will respond to chemotherapeutic treatment. In particular, there is a need for prognostic methods that reliably screen for subjects that will benefit from chemotherapy treatment.

THE SUMMARY OF THE DISCLOSURE

The present disclosure is based on diagnostic and prognostic methods for predicting or identifying subjects who will respond to treatment with low dose cyclophosphamide (or an analogue, derivate or active metabolite thereof). In particular, the present disclosure is based on the surprising finding that CC chemokine receptor 4 (CCR4) expression on T effector cells (Teff) from a subject with gynaecological cancer can selectively identify subjects who will respond to treatment with low dose cyclophosphamide.

Without wishing to be bound by theory, the inventors have shown that treatment with cyclophosphamide enriches the ovarian cancer environment in effector CD4 and CD8 T cells so that their activity can be enhanced locally at the tumour site, for example, by use of checkpoint inhibitors.

The present disclosure provides both diagnostic and prognostic methods to identify a subset of so-called responder patients (i.e. patients who will respond to cyclophosphamide). The methods are based on the finding that CCR4 up-regulation in effector CD4 and CD8 T cells is associated with better survival outcomes in subjects with gynaecological cancer, for example ovarian cancer.

The diagnostic methods (referred to herein as CCR4 up-regulation pre-treatment (CUP diagnostic)) can be used to identify responder patients early after receiving low dose cyclophosphamide (LDCy). The prognostic methods (referred to herein as CUP prognostic) can be used to identify responder patients before receiving LDCy. Both tests are based on detecting specific CCR4 upregulation on effector CD4 and CD8 T cells but not on regulatory T cells (Tregs). These methods identify subjects whose beneficial effector T cells will migrate into tumours following LDCy treatment. Such subjects can then be treated with, for example checkpoint inhibitors that prevent those beneficial effector T cells from being turned off within the tumour environment by Tregs.

Most CD8 T cells and CD4 T helper 1 ($T_H1$) cells memory effector cells do not normally express CCR4. Thus, without external intervention, suppressive CCR4+ Tregs are preferentially recruited to the tumour microenvironment, rather the beneficial CD8 T cells or $T_H1$ cells.

In particular, the present inventor has found that cyclophosphamide status can be useful for identifying cancer subjects who will respond to cyclophosphamide treatment, including with an analogue or derivative thereof.

Accordingly, in one aspect, the present disclosure provides a method for identifying a cancer subject who will clinically respond to treatment with cyclophosphamide or an analogue or derivative thereof, the method comprising detecting expression of CCR4 on Teff cells from the subject following administration of at least one dose of cyclophosphamide, or an analogue, or derivative thereof, wherein upregulation of CCR4 expression on the Teff cells indicates that the subject will clinically respond to treatment.

In certain examples, the subject has undergone at least one cycle of cyclophosphamide treatment.

In one example, the subject has a gynaecological cancer. In another example, the subject has ovarian cancer.

In one example, the method identifies a subject who will respond to further treatment with low dose cyclophosphamide, or an analogue or derivative thereof. In one example, the method identifies a subject who will respond to one or more further doses of low dose cyclophosphamide.

In one example, the method comprises detecting expression of CCR4 on Teff and T suppressor cells (Tsupp), wherein upregulation of CCR4 expression on Teff but not Tsupp identifies a subject who will clinically respond to treatment with cyclophosphamide or an analogue, or derivative thereof.

In one example, the Teff cells are T helper and/or cytotoxic T cells. In a further example, the Teff cells are CD4+ and CD8+ T cells. In yet a further example, the Teff cells are CD4+CD25− T cells. In still yet a further example, the Teff cells are FoxP3−CD25−CD4+ (Tconv) and CD8+ T cells. In still yet a further example, the Teff cells are CD8+ T cells.

In one example, the Tsupp cells are regulatory T cells (Tregs).

In one example, the method comprises detecting upregulation of CCR4 expression on Teff and T supp cells from a subject who has previously been administered one more doses of low dose cyclophosphamide.

In one example, the Teff cells and Treg cells are CD3+ T cells. In one example, the T helper cells comprise one or more of the following $T_H1$ cells, $T_H2$ cells, $T_H9$ cells, $T_H17$ cells, $T_H22$ cells and $T_{FH}$ cells.

In one example, the CD8+ cells are also CD69+.

In one example, the method comprises detecting expression of CCR4 on Teff cells in a biological sample obtained from the subject.

In another example, the detecting comprises:
(i) contacting the Teff cells in a biological sample obtained from the subject with an agent that binds to CCR4 on the surface of Teff cells; and
(ii) measuring the level of expression of CCR4 on the cells,
wherein upregulation of CCR4 expression on the Teff cells is indicative that the subject will clinically respond to further in vivo treatment with cyclophosphamide or an analogue or derivative thereof.

In one example, the method further comprises isolating or purifying Teff cells from the biological sample.

In a further example, the method comprises comparing the level of expression of CCR4 measured according to step (ii) with the level of expression of CCR4 on Teff cells from the subject pre-treatment with cyclophosphamide. This can provide information as to the baseline CCR4 expression of the Teff cells.

In one example, the method further comprises obtaining a biological sample from the subject comprising Teff cells. Methods of obtaining a biological sample will be familiar to persons skilled the art. For example, a biological sample is a blood sample.

The biological sample containing Teff cells may be obtained from the subject at a suitable time following the at least one dose of cyclophosphamide. For example, the biological sample will be obtained at a time when the cyclophosphamide has had sufficient time to exert an effect of the subject's immune system, in particular the subject's Teff cells. In another example the biological sample is obtained following allowing sufficient time for any upregulation in expression of CCR4 on Teff cells to be detected. For example, the biological sample may be obtained from the subject days or weeks following a dose of low dose cyclophosphamide. For example, the biological sample may be obtained from the subject after at least seven, fourteen, eighteen, twenty, or twenty-eight days following the first dose of cyclophosphamide. The biological sample may be obtained 1, 2, 3, 4, 5, 6, 7, or 8 weeks following the first dose of cyclophosphamide.

In a further example, the method further comprises treating the subject with low dose cyclophosphamide if the subject is identified as one who will clinically respond to cyclophosphamide treatment.

The methods of the present disclosure can also be used to prophylactically identify subjects who will clinically respond to treatment with cyclophosphamide or an analogue or derivative thereof, such subjects not having previously received cyclosphosphamide.

In another aspect, the present disclosure also provides a method for predicting whether a cancer subject who has not previously received cyclophosphamide will clinically respond to treatment with cyclophosphamide or an analogue or derivative thereof, the method comprising detecting expression of CCR4 on Teff cells following in vitro exposure of the Teff cells present in a biological sample obtained from the subject to cyclophosphamide, or an analogue, or derivative thereof, wherein upregulation of CCR4 expression on the Teff cells following exposure is indicative that the subject will respond to treatment. In one example, the method further comprises detecting upregulation of CCR4 expression on the Teff cells.

In one example, the subject has a gynaecological cancer. The gynaecological cancer may be selected from the group consisting of uterine, endometrial, ovarian, cervical, vulval or vaginal cancer. In a particular example, the subject has ovarian cancer.

In one example, the method identifies a subject who will clinically respond to treatment with low dose cyclophosphamide or an analogue or derivative thereof.

In a further example, the subject is one who has previously received treatment with one or more of an anthracycline an anti-metabolite, a taxane or a targeted therapy. For example, the subject is one who has received treatment with one or more of the following agents including epirubicin, doxorubicin, paclitaxel, docetaxel, 5-fluorouracil, capecitabine, gemcitabine, vinorelbine, trastuzumab, lapatinib and bevacizumab.

In one example, the subject is refractory to a non-cyclophosphamide chemotherapy agent, e.g. a platinum agent.

In one example, the method comprises detecting expression of CCR4 on Teff and T suppressor cells (Tsupp), wherein upregulation of CCR4 expression on Teff but not Tsupp identifies a subject who will clinically respond to treatment with cyclophosphamide or an analogue, or derivative thereof.

In one example, the Teff cells are T helper and/or cytotoxic T cells. In a further example, the Teff cells are CD4+ and CD8+ T cells. In yet a further example, the Teff cells are CD4+CD25− T cells. In still yet a further example, the Teff cells are FoxP3−CD25−CD4+ (Tconv) and CD8+ T cells. In still yet a further example, the Teff cells are CD8+ T cells. In one example, the CD8+ T cells are also CD69+.

In one example, the Tsupp cells are regulatory T cells (Tregs).

In one example, the Teff and/or Tsupp cells are present within a biological sample obtained from the subject.

In one example, detecting expression comprises:
(i) exposing the biological sample to cyclophosphamide or an analogue or derivative thereof in vitro;
(ii) contacting the Teff cells in a biological sample from the subject with an agent that binds to CCR4 on the surface of Teff cells; and (iii) measuring the level of expression of CCR4 on the cells, wherein upregulation of CCR4 expression on the Teff cells is indicative that the subject will clinically respond treatment with cyclophosphamide or an analogue or derivative thereof.

In a further example, the in vitro exposure to cyclophosphamide or an analogue or derivative thereof is for a period of at least 24 hours, at least 48, or at least 72 hours. In one example, the in vitro exposure is for a period of about 1 day, about 2 days or about 3 days or greater than 3 days.

In a further example, the biological sample is exposed to mafosfamide, ifosfamide or trofosfamide in vitro. In a particular example the biological sample is exposed to mafosfamide in vitro.

In one example, the method comprises isolating or purifying Teff cells from the biological sample.

In a further example, the method comprises comparing the level of expression of CCR4 measured according to step (iii) with the level of expression of CCR4 on Teff cells from the subject pre-exposure to cyclophosphamide or an analogue or derivative thereof.

In another example, the method comprises comparing the level of CCR4 expression determined in step (iii) with the level of CCR4 expression on Teff cells from control subjects. In one example, a control subject(s) refers to the average CCR4 expression in Teff cells obtained from a pooled population of subjects with gynaecological cancer, more preferably ovarian cancer. In another example, the control subjects are chemotherapy naïve subjects.

In a further example, the method further comprises treating the subject with low dose cyclophosphamide if the subject is predicted to clinically respond to cyclophosphamide treatment.

The methods of the present disclosure can be used to identify or predict subjects who will respond to treatment with low dose cyclophosphamide. In one example, the subject has a cancer which can be treated with cyclophosphamide or an analogue, derivative or active metabolite thereof. In a further example, the subject has a cancer that secretes C—C motif chemokine 22 (CCL22).

For example, the subject's cancer may be selected from the group consisting of Hodgkin's and non-Hodgkin's lymphoma, Burkitt's lymphoma, chronic lymphocytic leukemia (CLL), chronic myelocytic leukemia (CML), acute myelocytic leukemia (AML), acute lymphocytic leukemia (ALL), T-cell lymphoma (mycosis fungoides), multiple myeloma, neuroblastoma, retinoblastoma, rhabdomyosarcoma, Ewing's sarcoma; breast, testicular, endometrial, ovarian, other gynaecological cancers including uterine, cervical, vulval or vaginal cancer, and lung cancer or a combination of any of these.

In a particular example, the subject has ovarian cancer.

In some examples, the subject has early stage cancer. In some examples, the subject has advanced-treatment refractory cancer.

The subject according to the present disclosure may be a human male or female. In one example the subject is an adult human subject (e.g. a subject 18 years or older).

The methods described herein preferably identify or predict subjects who will respond to treatment with low dose cyclophosphamide or an analogue, derivative or active metabolite thereof. The duration of treatment will typically be determined by the treating physician. The term "low dose cyclophosphamide" is a dosage which will be understood by the treating physician. In one example, low-dose cyclophosphamide refers to doses as described herein in the examples.

Without wishing to be bound by theory, low-dose cyclophosphamide is understood to refer to a dose of chemotherapy that provides a clinical benefit to the subject while avoiding some or all of the side effects of that agent when administered at a toxically high dose. In one example, low dose cyclophosphamide refers to a dose of between 25 and 50 mg administered orally twice daily.

In further examples according to the methods described herein, upregulation of CCR4 expression on Teff cells in detected in a biological sample comprising such cells. The biological sample is preferably any sample in which effector T cells reside, including but not limited to bone marrow, spleen, lymph nodes, Peyer's patches, mucosal associated lymphoid tissue, gut-associated lymphoid tissue, or blood. In a further example, the biological sample is a blood sample, such as a whole blood or serum sample. In a further example, the biological sample comprises peripheral blood mononuclear cells (PBMC).

In another example, the biological sample is ascites. In another example, the sample is tumour infiltrating lymphocytes (TILS) from the cancer affected organ. In some examples the biological sample is pre-treated to remove red blood cells. If the biological sample is an organ, a spleen biopsy, a cell suspension may be prepared from the tissue by use of mechanical means (e.g. teasing the tissue apart with tweezers). Further means, such as centrifugation may be employed to concentrate the cells. In other examples, the sample may be treated to remove extracellular matrix components and the like from the tissue.

In some examples, the biological sample is cryopreserved and stored for later analysis.

Detection of CCR4 expression on Teff cells may be carried out in vivo or in vitro.

In another example, according to any method described herein, the method further comprises:

(i) obtaining a biological sample from the subject, said biological sample comprising effector T cells; and (ii) preparing a cell suspension from the biological sample.

In some examples, the biological sample may be purified or enriched for lymphocyte cells (e.g. Teff cells). For example, sorting procedures (e.g. FACS) may be employed to remove non desirable cells such as macrophages, dendritic cells and B-cells. In one example, the cells are sorted based on expression of CD3. In another example, B cells are negatively sorted based on their expression of B cell markers (e.g. B220). In another example, the cells may be purified using magnetically labelled beads (e.g. Dynabeads).

The biological sample may comprise an heterogeneous population of cells within which at least a proportion of the T cells are T effector cells. For example, the population of cells may comprise at least 1%, at least 5%, at least 10%, at least 25%, at least 30%, or greater T effector cells. In another example, the biological sample may comprise a purified or enriched population of T effector cells. For example, the population of cells may comprise at least 20%, at least 30%, at least 60%, at least 70% or greater effector T cells.

Detecting the expression of CCR4 on cells can be performed according to methods known in the art. In one example, detecting expression of CCR4 on cells is performed by flow cytometry.

Measuring upregulation of CCR4 expression may be qualitative or quantitative. The difference in level of CCR4 expression can be expressed as an absolute value, a ratio or fold change depending on the method used.

In one example according to any method described herein, the Teff cells comprise $CD4^+$ and/or $CD8^+$ T cells. In one example, the CD4+ cells are T helper 1 ($T_H1$) or $T_H2$ cells. In some examples, the cells comprise CD4+ effector T cells. In some examples, the sample of cells comprise CD8+ effector T cells. In another example, the cells comprise conventional T (Tconv) cells. In a further example, the Tconv comprise CD4+ $T_H1$ Tcells and/or CD8+ cytotoxic T cells. In a further example, the Teff comprise CD25−CD4+ cells. In a further example, the Teff comprise FoxP3−CD25−CD4+ cells. In a further example, the Teff comprise CD8+ cells. In a further example, the Teff comprise CD8+CD69+ cells. In another example, the Teff cells comprise a combination of FoxP3−CD25−CD4+ cells and CD8+ T cells.

In some examples, upregulation of CCR4 expression is determined quantitatively or qualitatively. In some examples, upregulation of CCR4 expression is determined by comparing the expression level of CCR4 in Teff cells from the same subject before and after treatment in vivo with cyclophosphamide or an analogue, derivate or active metabolite thereof.

In some examples, upregulation of CCR4 is determined by comparing the expression level of CCR4 in Teff cells from the same subject before and after in vitro exposure to cyclophosphamide or an analogue, derivate or active metabolite thereof.

In some examples, CCR4 expression on Teff cells may be determined after each cycle of cyclophosphamide treatment. In another example, CCR4 expression on Teff may be determined at a given time point(s) if the subject is receiving continuous daily cyclophosphamide. For example, biological samples containing Teff cells may be obtained from the subject every 7 days, every 14 days or monthly to monitor the effectiveness of the cyclophosphamide treatment. If the expression level of CCR4 decreases over time, this would alert the clinician that the subject is not responding and that they should investigate alternative forms of treatment, including for example, alternative chemotherapy agent(s). Accordingly, in some examples, the method does not require comparison to a baseline or pre-treatment level. The expression of CCR4 on Teff cells may be compared between cycles of low dose cyclophosphamide or at given intervals in time if the subject is receiving continuous low dose cyclophosphamide.

In some examples, the biological sample comprising Teff cells is obtained from the subject at any time prior to administration of the at least one dose of cyclophosphamide, or an analogue, or derivative thereof, or prior to exposure (in the case of in vitro assays) of the biological sample to cyclophosphamide, or an analogue, or derivative thereof, to provide a pre-treatment or baseline level of CCR4 on the Teff cells.

In one example, the baseline sample is obtained at least 30 days, at least 20 days, at least 15 days, at least two weeks, at least one week, or less than one week prior to administration of the at least one dose of cyclophosphamide, or an analogue, or derivative thereof, or prior to exposure to cyclophosphamide, or an analogue, or derivative thereof.

In regard to the prognostic methods described herein, a biological sample may be obtained from the subject any time prior to in vitro exposure of the sample to cyclophosphamide or an analogue or derivative thereof. In some examples, the biological sample may be obtained at least two weeks before, a week before, at least 72, 48, 24 hours or less, prior to in vitro exposure of the sample to cyclophosphamide or an analogue or derivative thereof. In some examples, the biological sample has been previously cryopreserved and stored for analysis at a convenient time.

In regard to the diagnostic methods described herein, the present methods provide for the identification of low dose cyclophosphamide responders in subjects receiving low-dose cyclophosphamide therapy according to any protocol. In some examples, the subject has received two doses, three doses, four doses, five doses or more of cyclophosphamide prior to obtaining the biological sample from the subject. In one example, the biological sample is obtained from a subject who is undergoing a treatment protocol with low dose cyclophosphamide. In one example, the biological sample is obtained from a subject who is receiving a cycle of low dose cyclophosphamide. In another example, the biological sample is obtained from a subject who is between cycles of low dose cyclophosphamide treatment but has received at least one dose of low dose cyclophosphamide.

In some examples, expression of CCR4 on Teff cells is upregulated at least 1.5, 2, 3, 4, 5, 6, 7-fold or greater compared to a suitable control, pre-treatment or baseline level of CCR4 expression.

In some examples, a ratio of CCR4 expression level on cytotoxic T cells and/or helper T cells (i.e. Teff cells) compared to CCR4 expression level on regulatory T cells can be used to identify or predict a subject who will respond positively to cyclophosphamide, or an analogue, derivative or active metabolite thereof.

In some examples, the ratio of CCR4 expression on cytotoxic T cells and/or helper T cells (i.e. Teff cells) is increased least two-fold, or least three-fold, or at least four-fold or greater relative to CCR4 expression on Tregs. In another example, CCR4 expression on CD4+ T cells (conventional T cells; Tconv) is increased at least two-fold, or at least three fold compared to Tregs. In another example, CCR4 expression on CD8+ T cells is increased at least three fold, or at least four fold compared to Tregs.

In another example, CCR4 upregulation may be expressed as a percentage. For example, CCR4 expression may be increased by 5%, 10%, 15%, 20%, 50%, 80%, 100%, 200%, 300%, 400%, 500% or 600% or greater compared to Tregs.

The methods described herein further include the step of treating the subject if the subject is identified as one who will clinically respond to cyclophosphamide.

Persons skilled in the art will appreciate that a number of different protocols are available for treating a patient with low dose cyclophosphamide. The scheduling and duration of treatment will generally be at the clinician's discretion and may depend on factors including the subject's age and the stage of cancer. For example, the subject may receive metronomic low dose cyclophosphamide chemotherapy. By metronomic chemotherapy it is meant repeated administration at a low dose frequently and without a long drug-free period. For example, the cyclophosphamide may be administered for three consecutive days, for 14 consecutive days or for 30 or greater consecutive days.

In a further example, the subject may receive cyclic low dose cyclophosphamide. The subject may receive any number of treatment cycles, for example, between 2 and 10, between 3 and 8, between 4 and 6. Alternatively, the subject may receive 4, 5, 6, 7, 8, 9, 10, 11, 12, 14, 15, 16, 18, 20 or greater treatment cycles.

In other examples, the subject may receive low dose cyclophosphamide for a continuous period of at least 3 to 7 days followed by a break of a given period, for example, one to two weeks. In one example, the subject may receive low dose cyclophosphamide in treatment cycles at fortnightly intervals. For example, a subject may receive 3 days of continuous daily cyclophosphamide at fortnightly intervals.

The cyclophosphamide may be administered to the subject either systemically or orally. Systemic forms of administration include direct intravenous injection or intravenous infusion.

In one example, the method comprises treating the subject with low dose cyclophosphamide in a therapeutically effective amount. In a further example, the cyclophosphamide is administered in an amount sufficient to provide an immune modulating effect.

The subject may receive low dose cyclophosphamide as a single dose or divided dose. In one example, the subject may receive a dose of between 50 and 300 mg cyclophosphamide daily. In one example, the administration is 50 mg twice per day (morning and evening) orally.

The present disclosure also provides a method for assessing the efficacy of low dose cyclophosphamide treatment of a cancer subject, the method comprising detecting in a first biological sample comprising Teff cells at a first time point, the level of expression of CCR4, repeating this analysis with a second biological sample comprising Teff cells at a later time point, and comparing the level of expression of CCR4 at the two time points wherein upregulation of CCR4 expression on Teff cells in the second sample compared to the first is indicative of clinically effective treatment.

In one example, the first time point is before or after the subject has received at least one dose of cyclophosphamide, or an analogue or derivative thereof.

The present disclosure also provides a monitoring method for assessing the regression or progression of ovarian cancer in a subject, the method comprising detecting in a first biological sample comprising Teff cells at a first time point, the level of expression of CCR4, repeating this analysis with a second biological sample comprising Teff cells at a later time point, and comparing the level of expression of CCR4 at the two time points wherein upregulation of CCR4 expression on Teff cells in the second sample compared to the first is indicative of regression of ovarian cancer.

In one example, the first time point is before or after the subject has received at least one dose of cyclophosphamide, or an analogue or derivative thereof. In one example, the first time point is pre-treatment or baseline and the second time point is following cyclophosphamide treatment. In another example, both the first and second time points are following cyclophosphamide treatment in the subject.

In some examples, the level of CCR4 expression is compared to a baseline level of CCR4 expression obtained from healthy (non-cancerous) subjects. In other examples, expression of CCR4 on Teff can be measured prior to each cycle of cyclophosphamide to monitor the subject's cyclophosphamide response.

In some examples, the methods described herein further comprise administering a therapeutic agent to the subject selected from the group consisting of a checkpoint inhibitor(s), an anti-cancer vaccine(s), a monoclonal antibody, an additional chemotherapeutic agent(s), a cytokine, an oncolytic virus, chimeric antigen receptor (CAR) T-cell therapy, and an immunomodulatory agent(s) or a combination of any of these. The check-point inhibitor may be one which targets PD-1 or PD-L1 (e.g. PD-1 or PD-L1 inhibitor). In one example, the PD-1 or PDL-1 is selected from the group consisting of pembrolizumab (keytruda), nivolumab (opdivo), and atezolizumab (Tecentriq). In one example, the checkpoint inhibitor is an agent that targets CTLA-4.

In another example, the additional chemotherapeutic agent is selected from the group consisting of adriamycin, vincristine, doxorubicin, carboplatin, or methotrexate or a combination thereof.

In one example, the immunomodulatory agent is selected from the group consisting of lenalidomide and pomalidomide or a combination thereof.

The methods described herein can also be used in a method for treating cancer in a subject.

In another aspect, the present disclosure also provides a method for treating a gynaecological cancer in a subject in need thereof, the method comprising:
(i) performing a method described herein to identify or predict a subject who will respond to low dose cyclophosphamide; and
(ii) administering further low cyclophosphamide to the subject if the subject is identified or predicted to be one who will clinically respond to treatment with low dose cyclophosphamide.

In one example, the method further comprises:
(i) contacting the Teff cells in a biological sample obtained from the subject with an agent that binds to CCR4 on the surface of Teff cells; and
(ii) measuring the level of expression of CCR4 on the cells.

In one example, the method further comprises isolating or purifying Teff cells from the biological sample.

The present disclosure also provides a method of treating an ovarian cancer subject with low dose cyclophosphamide, the subject having previously been identified or predicted to respond to low dose cyclophosphamide according to a method described herein.

In another aspect, the present disclosure provides a method of treating ovarian cancer in a subject in need thereof, the method comprising:
(i) detecting expression of CCR4 on Teff cells from the subject following administration of at least one dose or cycle of cyclophosphamide treatment, or an analogue, or derivative thereof;
(ii) measuring the level of upregulation of CCR4 expression of the Teff cells;
(iii) administering further low cyclophosphamide to the subject if the subject has upregulation of CCR4 expression on their Teff cells The present disclosure also provides a complex comprising Teff cells and a CCR4 binding moiety bound thereto for use, or when used in a method for identifying or predicting a subject who will respond to low dose cyclophosphamide according to a method described herein.

The methods disclosed herein may be used in combination with other screening methods to identify cancer subjects based on expression of one or more biomarkers that are positively correlated with a given cancer. In one example, the biological sample obtained from the subject may be further screened for one or more biomarkers which are over-expressed in ovarian cancer, wherein the biomarker is selected from the group consisting of HE4, CA125, glycodelin, MMP-7, Muc-1, PAI-1, CTHRC1, inhibin A, PLAU-R, prolactin, KLK-10, KLK-6, SLPI, alpha-1 antitrypsin, Imp-2, MAL2, Cox-1, protein kinase C-iota, cadherin-6, ADPRT, matriptase, folate receptor, claudin 4, mesothelin, aquaporin 5, cofilin 1, gelsolin, clusterin, alpha tetranectin, vitronectin, PAPP-A and folistatin.

The present disclosure also provides a kit comprising reagents for detecting CCR4 expression on Teff cells for use or when used in any of the methods described herein. In one example, the kit comprises a container into which the biological sample is collected, and one or more binding reagents that bind to a surface antigen selected from the group consisting of CD3, CD8, CD4, CD25, CCR4 and FoxP3.

Optionally, any of the methods provided herein may be used in conjunction with any other known methods, particularly a known diagnostic, prognostic, predictive, and/or monitoring method for cancer.

In some examples, the methods and kits of the present disclosure advantageously permits stratification of cancer patients. This allows a more optimal anti-cancer treatment or regime to be identified for a given individual subject. This also allows adjustments to the treatment regime to be made in light of changes to CCR4 levels within the first cycle of treatment. In some embodiments, the methods and kits of the present disclosure advantageously permits prediction, stratification, and/or monitoring via a test for a biomarker which can be carried out on a readily obtainable sample such as a blood sample.

DETAILED DESCRIPTION OF THE DISCLOSURE

Figure 2:
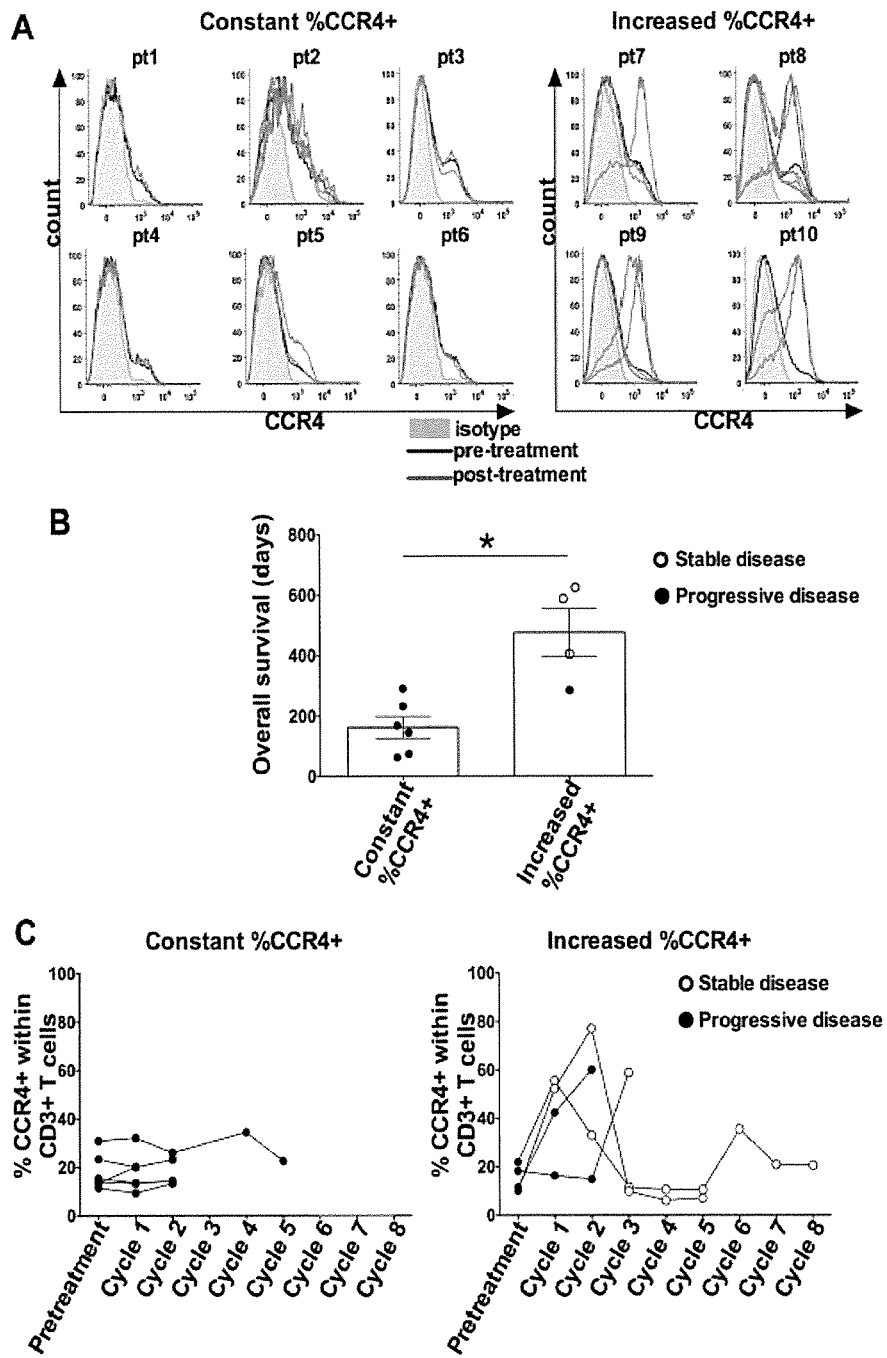
FIG. 2 Cyclophosphamide increases CCR4 expression on T cells. Peripheral blood mononuclear cells (PBMCs) were obtained from cancer patients pre-treatment and following each cycle of treatment with 50 mg of oral cyclophosphamide, taken twice daily for 3 consecutive days. The expression of CCR4 on T cells was determined using flow cytometry. Changes in CCR4+ T cell frequency were determined and 4 patients showed significant increases in the frequency of CCR4+ T cells following treatment. (A) the expression of CCR4 on CD3+ T cells was compared between patients that had no change in the frequency of CCR4+ T cells following treatment (constant % CCR4, n=6) and patients that had a significant increase in the frequency of CCR4+ T cells at least once after treatment (increased % CCR4, n=4). (B) the overall survival was also compared between the two patient groups. (C) the time-points when increases in the frequency of CCR4+ T cells, and disease stability occurred. * represents $p<0.05$ statistical significance in fold change from pre-treatment levels and graphs show means±standard error of the mean (SEM).

Unless defined otherwise, all technical and scientific terms used herein have the same meanings as commonly understood by one of ordinary skill in the art to which this disclosure belongs. Any materials and methods similar or equivalent to those described herein can be used to practice or test the present disclosure. Practitioners are particularly directed to Ausubel et al., Current Protocols in Molecular Biology, Supplement 47, John Wiley & Sons, New York, 1999; Colowick and Kaplan, eds., Methods In Enzymology, Academic Press, Inc.; Weir and Blackwell, eds., Handbook of Experimental Immunology, Vols. I-IV, Blackwell Scientific Publications, 1986; Remington's Pharmaceutical Sciences (18th ed., Mack Easton, Pa. (1990)), for definitions and terms of the art and other methods known to the person skilled in the art.

Throughout this specification, unless specifically stated otherwise, or the context requires otherwise, reference to a single step, composition of matter, group of steps or group of compositions of matter shall be taken to encompass one and a plurality (i.e., one or more) of those steps, compositions of matter, group of steps or group of compositions of matter.

Those skilled in the art will appreciate that the disclosure described herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions and methods are clearly within the scope of the disclosure.

Any example disclosed herein shall be taken to apply mutatis mutandis to any other example unless specifically stated otherwise.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "and/or", e.g., "X and/or Y" shall be understood to mean either "X and Y" or "X or Y" and shall be taken to provide explicit support for both means or for either meaning. Furthermore, a list or features including the phrase "and/or" between the second last and last feature means that any one or more of the listed features may be present in any combination.

Reference to the singular forms "a", "an" and "the" is also understood to imply the inclusion of plural forms unless the context dictates otherwise.

As used in this disclosure, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B.

As used in this specification and the appended claims, terms in the singular and the singular forms "a," "an" and "the," for example, optionally include plural referents unless the content clearly dictates otherwise.

Unless otherwise stated, reference to the term "cyclophosphamide" as used herein also includes analogues, derivatives or active metabolites of cyclophosphamide.

As used herein, the term "about", unless stated to the contrary, refers to +/−10%, more preferably +/−5%, more preferably +/−1%, of the designated value.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Selected Definitions and Phrases

The term "subject" as used herein refers to a mammal including human and non-human animals. More particularly, the mammal is a human. Still more particular, the subject is a female. Terms such as "subject", "patient" or "individual" are terms that can, in context, be used interchangeably in the present disclosure. In certain examples, the subject may be an adult or a child (paediatric) subject. The term "adult" as used herein is understood to mean a human subject of age 18 years or greater. The subject may be an adult human subject between the ages of 60 and 85 years of age.

The term "low dose cyclophosphamide" is intended to mean a dose that is active in suppressing cancer in the subject but with minimal side effects. What constitutes low dose cyclophosphamide will typically be at the physician's discretion and the term is not intended to be limited to a particular dose. Clinically, low dose cyclophosphamide is understood to refer to an oral dose of about 1.2-2 $g/m^2$ or an oral dose of about 25-150 mg per day.

The term "dose" as used herein refers to a single administration of a given quantity of cyclophosphamide.

The term "measuring the level of expression" as used herein is intended to have a broad meaning and can encompass either qualitative or quantitative measurements. Method for measuring the level of expression are discussed elsewhere herein. By way of example, expression of CCR4 on Teff cells can be determined quantitatively by measuring the log (or linear) increase in fluorescence intensity between cells which are positive for a given marker and a suitable isotype or other appropriate control. The data can be represented as a histogram in which the mean fluorescence intensity (represented by the peak on the histogram) is compared with the mean fluorescence intensity of the control. A shift to the right along the X-axis of the histogram indicates positive staining and thus expression of the marker.

The term "treatment" or "treating" as used herein refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease are mitigated or eliminated. The treatment is preferably an anti-cancer treatment. Reference herein to "anti-cancer treatment" includes any treatment directed at treating cancer. The treatment may involve surgery, chemotherapy radiation and/or drugs.

As used herein, the term "treating cancer" is not intended to be an absolute term. In some aspects, the methods of the disclosure seek to reduce the size of a tumour or number of cancer cells, cause a cancer to go into remission, or prevent growth in size or cell number of cancer cells. In some circumstances, "treating cancer" leads to an improved prognosis and/or survival.

As used herein, the term "prognosis" refers to risk prediction of the severity of disease or of the probable course and clinical outcome associated with a disease, preferably cancer. It encompasses methods by which the skilled person can estimate and/or determine a probability that a given outcome will occur. The outcome to which the prognosis relates may be morbidity and/or mortality. In particular, the prognosis may relate to "progression-free survival" (PFS), which is the length of time that a patient lives with the disease without the disease progressing. Thus, PFS may be the time from the start of therapy to the date of cancer progression, or the time from the end of therapy to the date of cancer progression. The prognosis may relate to overall survival. By "overall survival" (OS) is meant the length of time that a patient lives with the disease before death occurs. Overall survival may, for example, be defined as the time from diagnosis of the cancer, treatment start, or treatment completion, until death. Overall survival is typically expressed as an "overall survival rate", which is the percentage of people in a study or treatment group who are still alive for a certain period of time after they were diagnosed with, or started treatment for, or completed treatment for, a disease, such as cancer. The overall survival rate may, for example, be stated as a five-year survival rate, which is the percentage of people in a study or treatment group who are alive five years after their diagnosis or the start or completion of treatment.

Statistical information regarding the average (e.g. median, mean or mode) OS and PFS of patients having a particular type of cancer is available to those skilled in the art. A determination whether a subject has, or is likely to have, an increased or decreased OS or PFS compared to such an average may therefore be made.

As used herein, the term "increased survival" refers to an increase in lifespan or quality of life of a subject suffering from a disease such as cancer. For example, increasing survival also includes promoting cancer remission, preventing tumour invasion, preventing tumour reoccurrence, slowing tumour growth, preventing tumour growth, decreasing tumour size, decreasing total cancer cell counts and the like.

By "progressing" or "progression" is meant that the disease gets worse, i.e. that the severity increases, for example that the tumour burden increases, that the tumour increases in size and/or weight, that the cancer becomes malignant or more malignant, and/or that metastasis develops or the incidence and/or rate of metastasis increases.

By "regressing" or "regression" is meant that the disease improves, i.e. that the severity decreases, for example that the tumour burden decreases, that the tumour decreases in size and/or weight or becomes undetectable, that the cancer becomes less malignant, and/or that the incidence and/or rate of metastasis decreases.

The term "predict" or "predicting" as used herein refers to determining the likelihood of a particular outcome.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is used to refer to an amount necessary to effect treatment of a disease or condition as hereinbefore described. The effective amount may vary according to the disease or condition to be treated and also according to the weight, age, racial background, sex, health and/or physical condition and other factors relevant to the mammal being treated. Typically, the effective amount will fall within a relatively broad range (e.g. a "dosage" range) that can be determined through routine trial and experimentation by a medical practitioner. The effective amount can be administered in a single dose or in a dose repeated once or several times over a treatment period.

A "therapeutically effective amount" is at least the minimum concentration required to effect a measurable improvement of a particular disorder (e.g. cancer). A therapeutically effective amount herein may vary according to factors such as the disease state, age, sex, and weight of the patient, and the ability of the cellular composition to elicit a desired response in the individual. A therapeutically effective amount is also one in which any toxic or detrimental effects of the composition are outweighed by the therapeutically beneficial effects. In the case of cancer, a therapeutically effective amount can reduce the severity, inhibit or delay progression of cancer and/or relieve to some extent one or more of the symptoms associated with the cancer.

The term "ovarian cancer" as used herein in intended to mean those conditions classified by post-exploratory laparotomy as premalignant pathology, malignant pathology and cancer (FIGO stages 1-4). Staging and classification of ovarian cancer are described elsewhere herein. "Early-stage ovarian cancer" refers to those disease states classified as stage 1 or stage 2 carcinoma. Early detection of ovarian cancer significantly increases 5-year survival rates.

The term "identify a subject" as used herein may be used interchangeably with the term "screening a subject". These terms refer to strategies to identify subjects who have an increased likelihood of responding to cyclophosphamide, in particular low dose cyclophosphamide or an analogue, derivate or active metabolite thereof. The screening methods of the disclosure are not intended to definitively diagnose a subject as being a responder or non-responder. Rather, such methods are intended to identify subjects having an increased likelihood of responding to cyclophosphamide treatment. Such screening methods may be used in combination with one or more other methods used to definitively diagnose ovarian cancer or gynaecological cancer, including pelvic examination, transvaginal ultrasound, CT scan, MRI, laparotomy, laparoscopy and biopsy of tissue samples.

The term "biomarker" as used herein refers to any gene or protein whose level of expression in a tissue or cells is altered compared to that of a normal or healthy cell or tissue.

The term "stratification" or "stratifying" as used herein refers to the division of a population into subpopulations on the basis of a specified criteria. More particularly, it refers to the division of a cohort of subjects or patients into at least two groups on the basis of specific criteria, which in the context of the present application comprises or consists of CCR4 expression in a sample of cells.

The term "upregulated" or "upregulation of CCR4 expression" as used herein refers to a level of expression of CCR4 which is significantly or substantially greater following exposure to cyclophosphamide or an analogue, derivative or active metabolite thereof compared to the level of expression of CCR4 either in the absence of cyclophosphamide exposure or compared to a previous exposure to cyclophosphamide, including analogues, derivatives or active metabolite thereof. More particularly, it refers to a level of protein expression, and still more particularly, a level of cell surface protein expression.

The term "stable disease" as used herein means a cancer or tumour that is neither growing or shrinking.

The term "progressive disease" as used herein means a cancer or tumour that is worsening or spreading.

DETAILED DISCLOSURE

The present disclosure provides methods for screening or stratifying subjects, in particular cancer subjects for treatment with low dose cyclophosphamide based on upregulation of CCR4 expression on the subject's Teff cells.

The present inventors have found that treatment of cancer patients with low dose cyclophosphamide (LDCy) alters the comparative migration capabilities of beneficial Teff cells relative to T regulatory cells (Tregs) into the cancer microenvironment by altering their comparative CCR4 expression pattern. Based on this finding, the inventors have developed an immune prediction test (referred to as CCR4 up-regulation pre-treatment (CUP diagnostic)) that can be used to identify responder patients early after receiving low dose cyclophosphamide (LDCy). This test can thus identify patients who will receive the maximum benefit from cyclophosphamide treatment.

The inventors have found that subjects having increased expression of CCR4 on Teff cells is positively correlated with longer survival rates.

These findings are unexpected as earlier work had demonstrated that expression of CCR4 is increased in Tregs in certain cancers.

Typically, a sample of cells will be obtained from the subject to be assessed and the level of expression of CCR4 on Teff cells within the sample determined. An increase in expression (i.e. upregulation) of CCR4 following treatment with cyclophosphamide indicates that the subject has a greater likelihood of responding to cyclophosphamide or to further treatment cycles of cyclophosphamide. Steady levels of expression of CCR4 following treatment with the cyclophosphamide indicates that the subject is unlikely to respond to further treatment with this agent.

Additionally, responder patients can be identified prior to receiving treatment with LDCy (CUP prognostic). Thus, only those patients who are identified as responders can be selected for treatment with cyclophosphamide chemotherapy.

LDCy is currently used as second line treatment after patients have undergone other treatments, often having developed resistance to taxane or platinum drugs. In this setting it results in clinical benefit for 25-44% of patients ovarian cancer (Handolias, D., et al. (2013) Oral cyclophosphamide in recurrent ovarian cancer. Asia-Pacific journal of clinical oncology).

Administration of chemotherapy in low doses would be preferable due to a lowering of toxicity to the patient and/or frequency of adverse events. Furthermore, the availability of cyclophosphamide in oral form makes this agent particularly attractive for low resource settings (e.g. where there are no hospitals or getting to a hospital is difficult).

Currently, cyclophosphamide is given to ovarian cancer patients who are at an advanced or end stage. The ability to identify patients who will respond to cyclophosphamide treatment would be advantageous since it provides to patients who are identified as non-responders to be given alternative beneficial treatment without delay. Additionally, it would open the door to its use in first line therapy given its better tolerability in patients compared to platinum and taxane agents.

Moreover, the ability to identify responders has great potential to be rapidly used across the many other cancers where LDCy is a late-stage treatment option such as breast cancer. Additionally, the methods described herein would enable effective combinations of LDCy with other cancer therapies, e.g. checkpoint inhibitors. For example the methods described herein will identify patients whose beneficial immune cells will migrate into tumours following LDcy treatment, and the co-administration of checkpoint inhibitors would prevent these beneficial immune cells from being turned off within the tumour environment by immune suppressor cells such as Tregs.

Moreover, the use of LDCy upon first relapse (where it is not currently used) offers a powerful and low-toxicity treatment option for patients at the first evidence of sub-clinical recurrence (rising CA125 3 months post first-line platinum-based chemotherapy).

Effector T Cells

The methods of the present disclosure comprise detecting and/or measuring expression of CCR4 on effector T cells. The term "effector T cells" refers to T cells that have been activated in response to a stimulus. This class of T cells includes T helper cells and cytotoxic (killer) T cells.

Cytotoxic (killer) T cells are involved in the destruction of infected and transformed cells and therefore help protect the host from virus infections and cancer. Cytotoxic (killer) T cells have also been implicated in transplant rejection. These cells express the CD8 glycoprotein on their cell surface and are sometimes referred to as CD8+ T cells. Other cell surface markers found on Cytotoxic (killer) T cells include CD3 and αβ TCR. They are also positive for EOMES, T-bet and BLIMP1 transcription factors.

T helper cells ($T_H$) are promote and assist in immune response, in particular they have been described to help the activity of other T cells by releasing T cell cytokines. T helper cells include $T_H1$, $T_H2$, $T_H22$, $T_H17$, $T_H9$ and $T_{FH}$. These cells express the surface protein CD4 and are sometimes referred to as CD4+ T cells. Other cell surface markers include CD3 and αβ TCR. Additional markers expressed on $T_H$ cells include IL-12R, IFNγR, CXCR3, IL-17RB, an IL-1R. Accordingly, the Teff cells may also include one of more of these markers.

In one example, the Teff cells are T helper and/or cytotoxic T cells. In a further example, the Teff cells are CD4+ and CD8+ T cells. In yet a further example, the Teff cells are CD4+CD25− T cells. In still yet a further example, the Teff cells are FoxP3−CD25−CD4+ (Tconv) and CD8+ T cells. In still yet a further example, the Teff cells are CD8+ T cells. In one example, the CD8+ cells are also CD69+.

In one example, the Teff cells are CD3+ T cells. In one example, the T helper cells comprise one or more of the following $T_H1$ cells, $T_H2$ cells, $T_H9$ cells, $T_H17$ cells, $T_H22$ cells and $T_{FH}$ cells.

Regulatory T Cells

Regulatory T cells are formerly known as suppressor T cells and refer to a subpopulation of T cells which modulate the immune system, maintain tolerance to self-antigens and prevent auto-immune disease. Their function is to suppress or downregulate induction and proliferation of effector T cells (Bettelli E et al. (2006) Nature 441(7090):235-238.

Regulatory T cells are characterised by expression of CD4, CD25 and CD127. Regulatory T cells may also express CD3+FoxP3+CD25+CD4+. Regulatory T cells in human are characterised by a high level of expression of CD25.

Chemokines and Chemokine Receptors

CCR4 (also referred to as CC chemokine receptor 4 and chemokine (C—C motif) receptor 4) is a G-protein coupled receptor. CCR4 is the receptor for the chemokines—thymus and activation-regulated chemokine (also referred to as CCL17) and macrophage-derived chemokine (also referred to as CCL22) CCR4 is predominantly expressed on T-helper cell type 2 ($T_H2$) cells and regulatory T (Treg) cells. Limited expression of CCR4 occurs on other healthy cells and tissues, for example memory CD8+ T cells which secrete a combination of type 1 (interleukin (IL)-2, interferon (IFN)-γ and tumour necrosis factor (TNF) and type 2 (IL-4) cytokines (Kondo, T. & Takiguchi, M. (2009). International immunology 21, 523-532 (2009).

The CCR4 receptor enables T cells to migrate to sites of inflammation rich in its ligands CCL2, CCL4, CCL5, CCL17 and/or CCL22 (Cronshaw, D. G., Owen, C., Brown, Z. & Ward, S. G. (2004) Journal of immunology 172, 7761-7770). Ovarian cancer cells and macrophages that infiltrate tumour ascites secrete copious amounts of CCL22 (Yigit, R., et al. Cytokine analysis as a tool to understand tumour-host interaction in ovarian cancer. European journal of cancer 47, 1883-1889 (2011)). Without external intervention, suppressive CCR4+ Tregs are preferentially recruited to the tumour microenvironment, rather the beneficial CD8 T cells or $T_H1$ cells (CD4$^+$ effector cells).

The methods of the present disclosure comprise, or consist of determining expression of CCR4, in particular on effector T cells such as CD4+ and CD8+ T cells.

In ovarian cancer ascites, bioactive Tregs inhibit local effector T cell responses.

Figures 1, 6:
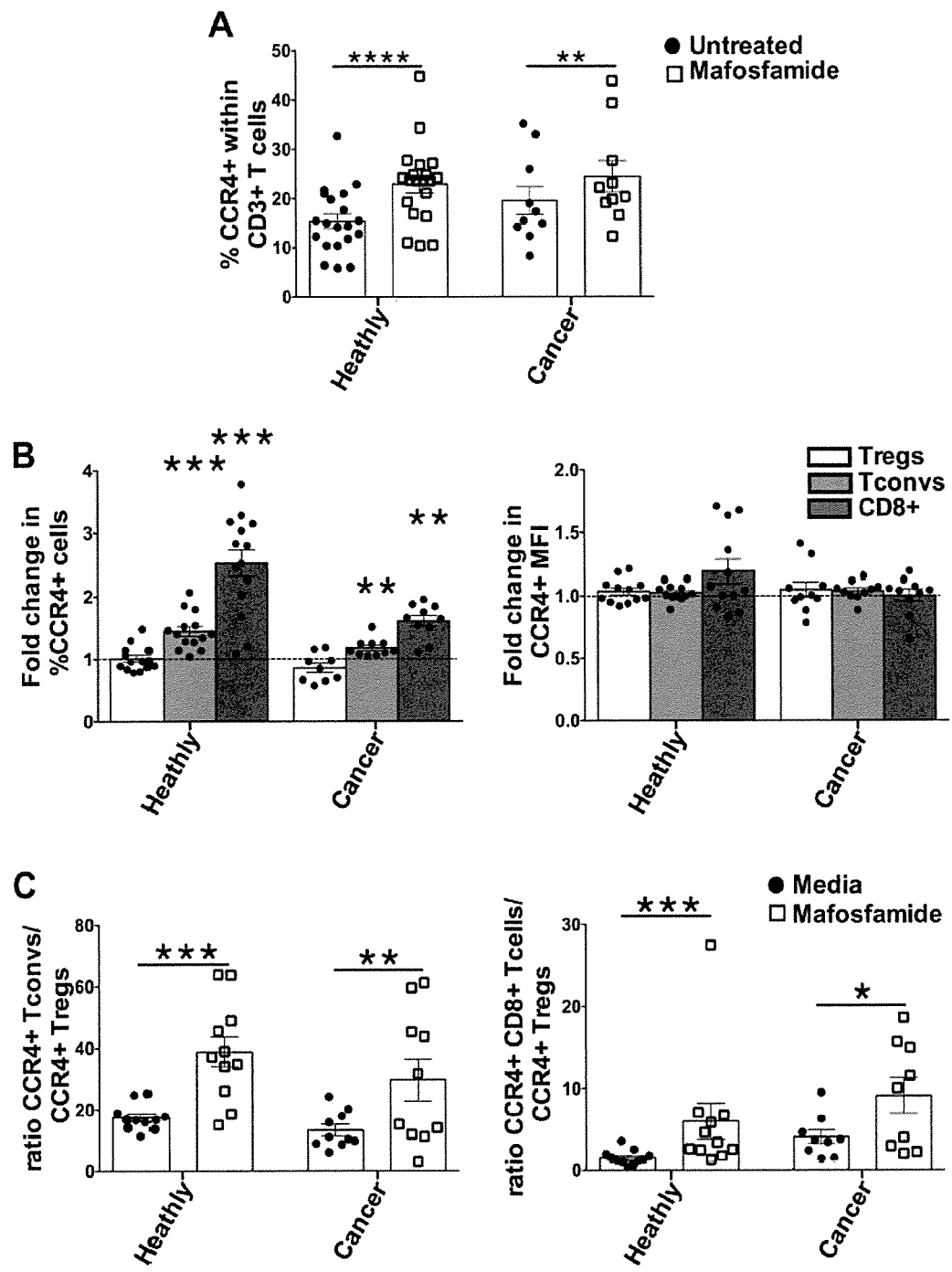
FIG. 1 shows the sequence of human CCR4.
FIG. 6 Mafosfamide induces the expression of CCR4 on T cells. Healthy donor and cancer patient pre-treatment PBMCs were cultured with or without 1.5 μg/ml of mafosfamide for 72 hours. A the expression of CCR4 on CD3+ T cells was then determined using flow cytometry and compared between untreated and mafosfamide treated cells (healthy donors n=20 and cancer patients n=10).  represents $p<0.01$ and  represents $p<0.0001$ statistical significance between treated and untreated cells. B the frequency of CCR4+ T cells as well as the MFI of CCR4 were then determined for Tregs, Tconvs, and CD8+ T cells and treated values normalised to untreated values (healthy donors n=14 and cancer patients n=10).  represents $p<0.01$ and *** represents $p<0.001$ statistical significance in fold change from untreated levels. C the ratios of Tconvs to Tregs and CD8+ T cells to Tregs were determined for mafosfamide treated cells and compared to that of untreated cells (healthy donors n=11 and cancer patients n=10). * represents $p<0.05$,  represents $p<0.01$ and * represents $p<0.001$ statistical significance between treatment groups. Graphs show means±standard error of the mean (SEM). D comparison of up-regulation in frequency of CCR4+ CD4 Tcell effectors between CCR4 steady (n=6) and CCR4 spike (n=4) patients ($p<0.0005$).
Figures 2, 6:
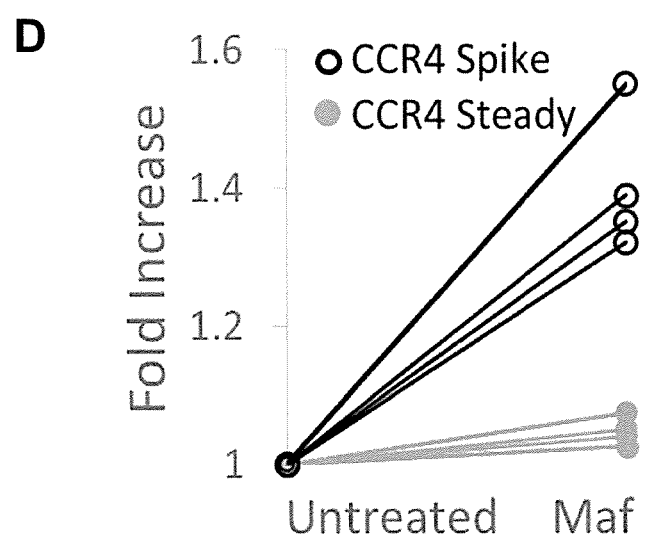

The sequence of human CCR4 is available on published databases. For example, the protein sequence of human CCR4 is available as UniProt reference P51679. A representative sequence is shown in FIG. 1.

Subjects

The methods and kits of the present application can be used to identify subjects will respond to treatment with a chemotherapeutic agent by determining the expression of CCR4 In some embodiments, the subject to be assessed has cancer. As used herein, "cancer" is a collective term for conditions characterised by neoplasia, i.e. the abnormal growth or division of cells. Cancerous cells may thus be referred to as "neoplastic". A collection of cancer cells is often referred to as a "tumour" and the terms "tumour" and "cancer" are used interchangeably herein. A tumour may be benign or malignant. Preferably, it is malignant.

The cancer may be any cancer, such as carcinomas, sarcomas, leukaemias, lymphomas, gliomas and the like. In some embodiments, the cancer is a carcinoma, sarcoma and/or glioma. In some embodiments, the cancer is a carcinoma.

Examples of suitable cancers include, without limitation, kidney cancer, ovarian cancer, pancreatic cancer, oesophagus cancer, cervical cancer, uterine cancer, bladder cancer, gallbladder cancer, liver cancer, head and neck cancer, squamous cell carcinoma, gastrointestinal cancer, breast cancer, prostate cancer, testicular cancer, lung cancer, non-small cell lung cancer, non-Hodgkin's lymphoma, Hodgkin's lymphoma, multiple myeloma, leukaemia, adult T cell leukaemia, laryngeal cancer, brain cancer, neuroblastoma, stomach cancer, endometrial cancer and melanoma.

In some embodiments, the cancer is a gynaecological cancer. As used herein, a "gynaecological cancer" is an uncontrolled growth and spread of abnormal cells that originate from the reproductive organs. Examples of gynaecological cancers include, without limitation, cervical, gestational trophoblastic disease (GTD), primary peritoneal, fallopian tube, placental, ovarian, uterine/endometrial, vaginal and vulval cancers. In some embodiments, the cancer is ovarian cancer.

Preferably, the cancer expresses CCL22. CCL22 (also referred to as macrophage derived chemokine or MDC) is a chemokine that is produced by tumour cells and tumour-infiltrating macrophages. CCL22 binds to CCR4 and is involved in chemotaxis of regulatory T cells (Tregs) into the tumour microenvironment which decreases anticancer immunity. Examples of cancers which express CCL22 include, but are not limited to, pancreatic cancer, hepatocellular carcinoma (HCC), gastric cancer, Lewis cell carcinoma, lung cancer, colorectal cancer, melanoma, prostate cancer, breast cancer and ovarian cancer.

The methods of the invention as described herein can be carried out on any subject which may suffer from cancer. The methods are generally carried out on mammals such as humans, other primates such as monkeys, laboratory mammals such as mice, rats, rabbits, guinea pigs, livestock mammals such as horses, cattle, sheep, pigs, or domestic pets such as cats, dogs. In some embodiments the subjects are humans. However, in other embodiments, the methods can be used in any appropriate animal model. A subject who is receiving medical attention may be referred to as a "patient". Any reference herein to a "subject" should therefore be understood to include reference to a patient, preferably a human patient.

In some embodiments, the subject may be showing evidence of relapse. In some embodiments, the subject may be showing evidence of first relapse In some embodiments, the subject may be showing evidence of sub-clinical recurrence. For example, in the case of ovarian cancer, the subject may have rising CA125 levels in the blood three months post first-line platinum-based chemotherapy. Accordingly, the methods of the present disclosure may increase the use of chemotherapeutic agents such as low dose cyclophosphamide upon first relapse (where it is not currently used). This would offer a powerful and low-toxicity treatment option for patients at the first evidence of sub-clinical recurrence.

The methods and kits of the present application can be used to identify subjects that will respond to treatment, either before therapy begins (in vitro incubation of drug with subject's blood/cell sample), or after therapy has started (in vitro blood/cell sample). For example, the subject may have started or be starting treatment with the chemotherapeutic agent. In some embodiments, the subject to be assessed has not be treated with the chemotherapeutic agent. In some embodiments, the subject may be being assessed to determine whether treatment with the chemotherapeutic agent is likely to improve survival. Therefore, the method includes incubating a sample of cells derived from the subject with the chemotherapeutic agent before CCR4 expression is determined. In some embodiments, the subject to be assessed has started therapy, for example, the subject to be assessed is within the first cycle of treatment with the chemotherapeutic agent. In this embodiment, the method includes determining CCR4 expression in a sample of cells derived from the subject being treated.

Ovarian Cancer

Ovarian cancer is the growth of abnormal malignant cells that begins in the ovaries. It is often associated with vague and non-specific symptoms such as bloating, pelvic or abdominal pain, difficulty eating and/or feeling full quickly and urinary symptoms. Once ovarian cancer has been diagnosed, cancer staging is performed to decide how far the disease has progressed.

Typically, staging of ovarian cancer involves taking samples of tissues from different parts of the pelvis and abdomen to determine whether to disease has spread and if so, how far it has spread. Ovarian cancer is staged using the International Federation of Gynaecology and Obstetrics (FIGO) staging system which describes four main stages:

Stage 1—The cancer is only found within the ovary (or ovaries) and has not spread to organs and tissues in the abdomen or pelvis, lymph nodes, or to distant sites.

Stage 2—The cancer has spread to other organs within the pelvis, for example the uterus, fallopian tubes, bladder, the sigmoid colon, or the rectum. It has not spread to lymph nodes or distant sites.

Stage 3—The cancer has spread beyond the pelvis to the lining of the abdomen and/or has spread to lymph nodes in the back of the abdomen (retroperitoneal lymph nodes).

Stage 4—The cancer has spread to the inside of the spleen, liver, lungs, or other organs located outside the peritoneal cavity.

The FIGO stage is an important predictor of long term survival. It is also used to help identify treatment options. Stage 4 is the most advanced form of ovarian cancer and is associated with the lowest five-year survival rate.

The methods of the present invention can be used in a subject having ovarian cancer at any clinical staging.

Biological Samples and Cells

The methods and kits of the present disclosure comprise determining expression of CCR4 in a biological sample obtained from a subject, preferably a cancer subject. The biological sample is any sample obtained from the subject in which Teff cells are present. As used herein, the term "obtained" is defined broadly and refers to cells, tissue or organs derived from a subject directly as well as cells, including those derived from the tissue or organ which have been cultured or proceed in some way.

In some examples, the biological sample selected from the group consisting of, but not limited to bone marrow, spleen, lymph nodes, Peyer's patches, mucosal associated lymphoid tissue, gut-associated lymphoid tissue, or blood. In some example, the cells comprise cells from a whole blood sample.

Biological samples may be obtained from a subject by a variety of techniques including, for example, by venepuncture, by scraping or swabbing an area or by using a needle to aspirate body fluids or tissues. Methods for collecting various biological samples are well known in the art.

In some examples, the cells are purified. As used herein, "purified" refers to cells that have been at least partially separated from other cell types with which they are normally associated in their naturally occurring state. Typically, the selected cell type is purified when it is at least 50% or 60%, by number, of total cells present. For example, the selected cell type is at least 75%, at least about 80%, at least about 85%, at least about 90%, at least about 91%, at least about 92%, at least about 93%, at least about 94%, at least about 95%, at least about 96%, at least about 97%, at least about 98%, at least about 99%, by number, of total cells present. The purity of the cells can be checked by flow cytometry and other suitable techniques.

In some examples, the cells comprise peripheral blood mononuclear cells (PBMCs). PBMCs can include lymphocytes (T cells, B cells, and NK cells), monocytes, and dendritic cells. PBMCs can be isolated from a whole blood sample using any technique known to the person skilled in the art. For example, PBMCs can be isolated via Ficoll density gradient centrifugation, cell preparation tubes (such as the BD Vacutainer® CPT) or SepMate tubes.

In some examples, the cells are selected based on expression of particular cell-surface markers. In some examples, the cells are selected based on cell-surface expression of CD3. In other examples, cells are selected based on expression of markers associated with T effector (Teff) cells or with T regulatory (Treg) cells.

For example, Treg cells include cells that express the cell surface proteins CD4, CD25 and CD27. In one example, the Treg cells are $CD27^{hi}$. In one example, the Teff cells are CD4+ or CD8+. In some examples, the Teff cells are CD25−CD4+ cells In some examples, Treg cells bear the surface markers CD3+FoxP3+CD25+CD4+. In some examples, the Teff cells are CD3+FoxP3−CD25−CD4+ cells (also referred to as Tconvs), In other examples, the Teff cells are CD3+CD8+ cells. In another example, the Teff cells are $CD69^+$ $CD8^+$. In another example, the Teff cells are CCR4+ CD8+ T cells or CCR4+ CD4+ T cells.

Cells can be selected based on cell surface expression using any technique known to the person skilled in the art. These techniques can be based on both positive and negative detection. In positive detection techniques the desired cells are labelled with antibodies and quantified. Suitable techniques for selecting cells based on cell surface expression of antigens include, but are not limited to, flow cytometry, immunoadsorption techniques, RosetteSep Whole Blood Based Cell Isolation and the like. In immunoadsorption techniques cells are selected with monoclonal antibodies and preferentially bound to a surface which can be removed from the remainder of the cells e.g. column of beads, flasks, magnetic particles. Example immunoadsorption techniques include, but are not limited to, Magnetic Antibody Based Cell Isolation such as Life Technologies Dynabeads® and Stemcell Technologies EasySep™, RoboSep™ and StemSep™.

The cells can be freshly obtained cells or cells that have been stored or cryopreserved. The cells can be cultured in suitable media before or after purification, for example in AIM-V media (Life Technologies, USA) with 5% normal human serum (HS, Sigma-Aldrich, USA) (complete AIM-V media).

Detecting and Measuring CCR4 Expression on Cells

The present inventor has found that low dose cyclophosphamide treatment increases effector $CCR4^+$ $CD8^+$ T cells in the blood but not CCR4+ Tregs. The methods and kits of the present disclosure comprise detecting upregulation of expression of CCR4 on Teff cells. Any method available in the art for the detection of CCR4 expression can be used in the methods of the present disclosure. In one example, expression of CCR4 is detected at a protein level. In some examples, detecting upregulation in CCR4 expression will prognostically identify subjects who will respond to cyclophosphamide treatment. In other examples detecting upregulation in CCR4 expression will diagnose subjects who will respond to further cycles of cyclophosphamide following prior cyclophosphamide treatment.

The term "upregulation of CCR4" as used herein refers to a level of expression of CCR4 on Teff cells which is substantially or significantly greater after exposure to, or administration of cyclophosphamide or an analogue or derivative thereof, compared to the level of CCR4 expression on Teff cells pre-treatment or pre-exposure to cyclophosphamide or an analogue or derivative thereof. In some methods, the term "upregulation of CCR4" may refer to a level of expression of CCR4 on Teff cells which is substantially or significantly greater between a first time point compared to a second time point where the subject has received cyclophosphamide at both time points.

In one example, significantly greater refers to a level which is greater than the standard error of the assessment method used. In one example, significantly greater refers to a statistical significance of $p<0.05$, $p<0.01$ or $p<0.001$.

In one example, detection of CCR4 is determined by measuring cell surface expression of CCR4 on T effector cells present in a biological sample. In a further example, the expression of CCR4 is measured by flow cytometry. In another example, expression of CCR4 is determined on Teff cells defined according to the cell surface expression profile discussed above. In one example, detection of CCR4 is determined on CD3+ T cells.

In another example, detection of CCR4 expression is determined on cells that are also CD8+ T cells. In another example, detection of CCR4 expression is determined on cells that are CD3+, CD8+ T cells. In another example, detection of CCR4 expression is determined on cells that are CD25−CD4+ cells. In another example, detection of CCR4 expression is determined on cells that are FoxP3−CD25−CD4+ cells. In another example, detection of CCR4 expression is also determined on cells that are FoxP3+CD25+CD4+ (i.e. Tregs) to confirm absence of upregulation of CCR4 on these cells.

In some examples, upregulation of CCR4 refers to an expression level of CCR4 which is at least 2 logs greater, at least 3 logs greater, at least 3.5 logs greater or at least 4 logs greater when assessed by flow cytometry.

In some examples, upregulation of CCR4 expression refers to an increase in the mean fluorescence intensity (MFI) of CCR4 observed by flow cytometry.

In some examples, upregulation of CCR4 expression refers to an expression level of CCR4 following cyclophosphamide treatment that is at least 2, 3, 4, 5, 6 or 7-fold or greater than the level of expression of CCR4 prior to cyclophosphamide treatment.

In some examples, upregulation of CCR4 expression level is at least 5%, at least 20%, at least 30%, at least 40%, at least 50%, at least 60%, at least 80%, at least 100%, at least 200%, at least 300% or greater following cyclophosphamide treatment compared to pre-treatment.

In some examples, upregulation of CCR4 expression level is at least 5%, at least 20%, at least 30%, at least 40%, or at least 50% or greater following exposure to mafosfamide compared to pre-treatment.

The skilled person will appreciate that the upregulation of CCR4 expression can be expressed a number of ways, including, but not limited to fold change in % CCR4+ cells or ratio of CCR4+ T conv/CCR4+ Tregs as shown in the examples herein.

In some examples, a threshold level of CCR4 above which it is considered to be upregulated in a biological sample may be established. Methods for selecting the threshold value include, but are not limited to analysis of ROC plot for CCR4 or analysis of the CCR4 expression level for a normal subject population. As used herein, the term "normal" refers to the level of expression in a corresponding biological sample from a healthy person who is not afflicted with cancer. Such a sample can be present in standardised form. Exemplary threshold or "cut-off" values include, the mean CCR4 expression level plus two standard deviations, as determined from a population of normal subjects; expression levels selected from the ROC curve that represent the highest value of sensitivity plus specificity; a level of expression of CCR4 that is statistically greater at p<0.05 than the level of CCR4 expression observed pre-treatment. Persons skilled in the art will appreciate that other methods for selecting appropriate threshold expression values can be used to practice the methods disclosed herein.

The upregulation of CCR4 expression is preferably observed following at least one cycle of cyclophosphamide treatment. In some examples, upregulation of CCR4 expression is observed following one, two or three cycles of cyclophosphamide treatment.

The present inventors have determined that subjects who will not respond to treatment with cyclophosphamide can be identified as having a level of expression of CCR4 that remains substantially the same at the level of CCR4 at baseline or pre-treatment. Accordingly, the present disclosure also provides a method for identifying a subject unlikely to respond to treatment with cyclophosphamide, analogue, derivative or active metabolite thereof, the method comprising determining expression of CCR4 on Teff cells from the subject, stable expression of CCR4 on said cells identifies a subject who will not respond to said treatment.

In this context, the term "stable expression" refers to an unchanged frequency in the level of CCR4 expression compared to pre-treatment or to subjects with an obvious increase in CCR4 expression (referred to as CCR4 spike subjects). In other words, there is no statistically significant difference in the level of CCR4 expression observed in the subject pre-treatment and post-treatment or pre-exposure and post-exposure to cyclophosphamide or an analogue, derivative or active metabolite thereof. In some examples, the CCR4 expression level remains stable after the first, second, third, fourth or further cycle of cyclophosphamide treatment.

Expression of CCR4 can be determined using any technique that can be used to identify and quantify cells expressing CCR4. For example, the amount of CCR4 may be determined by contacting a sample of cells derived from said subject with an antibody that binds to CCR4, subjecting the sample and the antibody to conditions which allow the antibody to bind and determining the amount of said chemokine in said sample. Any appropriate antibody can be used and examples of these are described elsewhere herein. For example, appropriate antibodies to CCR4, or antibodies which recognise particular epitopes thereof, can be prepared by standard techniques, e.g. by immunization of experimental animals, with the appropriate modifications made to the antibodies in terms of labelling etc. Examples of methods which may be used to determine expression of CCR4 include, but are not limited to, flow cytometry, immunoprecipitation, immunohistochemistry or staining of cells with antibodies, multiplex bead-based immunoassays, and Enzyme-Linked Immunosorbent Assay (ELISA).

Methods for assessing the efficacy of cyclophosphamide in a subject are also provided. Such methods typically comprise comparing the level of expression of CCR4 in a first biological sample procured prior to initiation of therapy (i.e. baseline or pre-treatment) with that from a second biological sample obtained following administration of at least a portion of therapy (e.g. one or more cycles of cyclophosphamide). A significantly or substantially higher level of expression of CCR4 in the second sample is a positive indication of the efficacy of therapy. A significantly or substantially lower level of expression of CCR4 is a negative indication of the efficacy of therapy. A used herein the term "a positive indication of the efficacy of therapy" means that the therapy is producing beneficial results in the treatment of the subject's cancer (e.g. tumour regression etc.). A "negative indication of the efficacy of the therapy" is intended to mean that the therapy is not having beneficial effects with respect to the treatment of the subject's cancer.

The present disclosure also provides a monitoring method for assessing the regression or progression of ovarian cancer in a subject, the method comprising detecting in a first biological sample at a first time point, the level of expression of CCR4 on Teff cells, repeating this analysis with a second biological sample obtained at a later time point, and comparing the level of expression of CCR4 on Teff cells at the two time points wherein upregulation of CCR4 expression on Teff cells between the first and second time points indicates regression of the ovarian cancer.

In one example, the first time point is pre-treatment or baseline and the second time point is following cyclophosphamide treatment. In one example, the first time point is following a first cycle of cyclophosphamide and the second time point is after a second or third cycle of cyclophosphamide. A significantly or substantially higher level of expression of CCR4 on Teff cells in the biological sample at the later time point indicates that the ovarian cancer has regressed. Whereas a significantly lower level of expression is an indication that the ovarian cancer has progressed. As used herein "regression of ovarian cancer" is intended to mean that the condition of the subject with respect to ovarian cancer has improved, as characterised by, for example, decreased tumour size. "Progression of ovarian cancer" means that the condition of the subject with respect to ovarian cancer has worsened, as characterised by, for example increased tumour size, metastasis etc.

The methods of the present disclosure may be used to predict whether a subject will respond to cyclophosphamide or an analogue, or derivative thereof before commencing treatment with cyclophosphamide or an analogue, or derivative thereof. For example, the prognostic methods can be performed using cells derived from subjects showing the first signs of recurrence, showing sub-clinical recurrence of their cancer, or subjects who have been formally diagnosed as having cancer. Such methods typically comprise comparing the level of expression of CCR4 on Teff cells in a first biological sample procured prior to exposure to cyclophosphamide with that of a second biological sample which has been exposed in vitro to mafosfamide. A significantly or substantially higher level of expression of CCR4 on Teff cells in the second sample is a positive indication that the subject will respond to cyclophosphamide treatment. A significantly or substantially lower level of expression of CCR4 is a negative indication that the subject with respond to cyclophosphamide treatment. In other words, the subject will not respond or will respond sub-optimally to cyclophosphamide treatment.

The present disclosure also provides a method of predicting whether a subject, who has not previously been treated with cyclophosphamide will respond to treatment with cyclophosphamide, or an analogue, or derivative thereof, the method comprising analysing effector T cells (Teff) from the subject for expression of CCR4, following in vitro exposure to cyclophosphamide, or an analogue, derivative or active metabolite thereof, wherein upregulation of CCR4 expression on said cells identifies a subject who will respond positively to cyclophosphamide treatment in vivo.

In one example, the analysis is performed on a biological sample comprising Teff cells.

Expression of CCR4 can be determined using any technique that can be used to identify and quantify cells expressing CCR4. In one example, the amount of CCR4 may be determined by contacting a sample of cells derived from said subject with any cell surface binding agent such as, for example a Fab, Fab', F(ab)2, F(ab')2 and variable domain fragment (dAb), variable heavy (VH) and variable light (VL) fragments; a peptide; an aptamer, a nanobody or other non-antibody affinity reagent. Antibodies may be monoclonal or polyclonal but in particular are monoclonal antibodies. The agent (e.g. antibody) may be derived from any source including animal (e.g. hamster, murine, rat, rabbit etc. or human or primate). The antibody may be partly or fully humanised.

In certain examples, expression of CCR4 is detected using an antibody. The term "antibody" broadly encompasses naturally occurring forms of antibody and recombinant antibodies such as single-chain antibodies, chimeric and humanised antibodies as well as antigen-binding fragments thereof. In some examples, the antibody is labelled with a detectable substance to facilitate detection in the biological sample. Examples of detectable substances include various enzymes, prosthetic groups, fluorescent materials, luminescent materials, bioluminescent materials and radioactive materials. Examples of suitable enzymes include horse radish peroxidase, alkaline phosphatase, beta-galactosidase, or acetylcholinesterase. Examples of suitable prosthetic group complexes include streptavidin/biotin and avidin/biotin. Examples of suitable fluorescent materials include fluorescein, rhodamine, phycoerythrin, and dansyl chloride.

In some examples, the methods of the present disclosure are practised using a commercially available antibody that binds to human CCR4. Examples of suitable commercial antibodies that bind to human CCR4 can be purchased from Lifespan BioSciences, Invitrogen, Enzo Lifesciences, Inc, Abcam, Miltenyi Biotec, Bio Legend, BD Biosciences, Santa Cruz Biotechnology, Inc and Abbexa Ltd.

Appropriate antibodies to CCR4, or antibodies which recognise particular epitopes thereof, can be prepared by standard techniques, e.g. by immunization of experimental animals, with the appropriate modifications made to the antibodies in terms of labelling etc. Examples of methods which may be used to determine expression of CCR4 include, but are not limited to, flow cytometry, immunoprecipitation, immunohistochemistry or staining of cells with antibodies, and Enzyme-Linked Immunosorbent Assay (ELISA).

Chemotherapy

Methods of the present disclosure can be used to identify subjects who will respond to cyclophosphamide or an analogue or derivative thereof. The methods of the present disclosure can also be used to predict whether a subject who has not previously received cyclophosphamide will respond to cyclophosphamide.

Ovarian cancer is a molecularly heterogeneous disease and molecular differences drive distinct clinical behaviours. Despite this, the main platinum/taxane-based chemotherapeutic treatments for ovarian cancer have failed to evolve over the last two decades, resulting in stagnant improvement in ovarian cancer survival, with an unchanged median five-year survival of approximately 40%. The involvement of over 12,000 women in phase III clinical trials has not changed the therapeutic landscape (Bookman, M A (2011) Eur J Cancer 47 S3).

Cyclophosphamide is a chemotherapeutic agent that has long been used to treat cancer (Arnold et al. (1958) Nature 181(4613):931) and autoimmune diseases. At high doses, it is immunosuppressive, while at low non-toxic doses it is an immune stimulant. Currently high dose cyclophosphamide is used as an immunosuppressant to treat autoimmune diseases such as lupus or conditioning for bone marrow transplants as it causes general lymphodepletion (Dussan et al. (2008) Lupus. 17(12):1079-85; Rossi et al. (2003) Bone marrow transplant. 31(6):441-6.). Low dose cyclophosphamide is used to treat cancer (Liu et al. (2010) J Immunother 33(1):53-9; Lutsiak et al. (2005) Blood. 105(7):2862-8; Ghiringhelli et al. (2007). Cancer Immunol Immunother 56(5):641-8; Kishimoto et al. (1990) Circulation. 82(3):982-9; Brodsky & Jones. (2008) Autoimmunity 41(8):596-600) and, compared to high dose cyclophosphamide, is generally well tolerated with significantly reduced risk of side effects.

LDCy is thus used as an immunotherapeutic in a variety of cancers. It is a member of the oxazaphosphorine family of mustard-alkylating agents. Cyclophosphamide is an inert prodrug. However, upon administration cyclophosphamide is hydrolysed by cytochrome enzymes P450 in the liver to its pharmacologically active form 4-hydroxycyclophosphamide, which exists in equilibrium with its tautomer, aldophosphamide (Clarke & Waxman (1989) Cancer Res 49(9): 2344-50; Yu et al. (1999) J. Pharm. Exp. Ther. 288(3):928-37). In the cytosol of target cells, the two products are converted, through spontaneous β-elimination, to phosphoramide mustard and acrolein (Brode & Cooke, (2008) Crit. Rev. Immunol. 28(2):109-26). Both metabolites are cytotoxic alkylating agents, while phosphoramide mustard also causes DNA cross-linking resulting in cell death.

In one example, the cyclophosphamide and its pharmaceutically acceptable salts, analogues, or derivatives thereof include, but are not limited to, cyclophosphamide, 4-hydroxycyclophosphamide, aldophosphamide, phosphoramide mustard, acrolein, mafosfamide, 4-hydroperoxycyclophosphamide, ifosfamide, trofosfamide and the like.

Chemotherapy Agents

In some embodiments, the methods further comprise administering an additional chemotherapeutic agent. The additional chemotherapeutic agent can be administered to the subject either prior to, substantially simultaneously with, or after treatment with the chemotherapeutic agent. In some embodiments, the chemotherapeutic agent is administered prior to the additional chemotherapeutic agent. In some embodiments, the additional chemotherapeutic agent is administered prior to the chemotherapeutic agent.

Throughout the specification "chemotherapeutic agent" and "cancer therapeutic agent" are used interchangeably. Examples of cancer therapeutic agents or chemotherapeutic agents include alkylating agents such as melphalan, chlorambucil, busulfan, thiotepa, ifosfamide, carmustine, lomustine, semustine, streptozocin, decarbazine, methotrexate, and mitomycin C; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.RTM.; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); thiotepa; taxoids, e.g. paclitaxel (TAXOL™, Bristol-Myers Squibb Oncology, Princeton, N.J.) and doxetaxel (TAXOTEPvE™, Pvhne-Poulenc Rorer, Antony, France); chlorambucil; gemcitabine; 6-thioguanine; mercaptopurine; methotrexate; platinum analogs such as cisplatin and carboplatin; vinblastine; trastuzumab, docetaxel, platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylomithine (DMFO); retinoic acid derivatives such as Targretin™ (bexarotene), Panretin™ (alitretinoin); ONTAKT™ (denileukin diftitox); esperamicins; capecitabine; and pharmaceutically acceptable salts, acids or derivatives of any of the above. Also included in this definition are anti-hormonal agents that act to regulate or inhibit hormone action on tumours such as anti-estrogens including for example tamoxifen, raloxifene, aromatase inhibiting 4(5)-imidazoles, 4-hydroxytamoxifen, trioxifene, keoxifene, LY 1 17018, onapristone, and toremifene (Fareston); and anti-androgens such as flutamide, nilutamide, bicalutamide, leuprolide, and goserelin; and pharmaceutically acceptable salts, acids or derivatives of any of the above. Further cancer therapeutic agents include sorafenib and other protein kinase inhibitors such as afatinib, axitinib, bevacizumab, cetuximab, crizotinib, dasatinib, erlotinib, fostamatinib, gefitinib, imatinib, lapatinib, lenvatinib, mubritinib, nilotinib, panitumumab, pazopanib, pegaptanib, ranibizumab, ruxolitinib, trastuzumab, vandetanib, vemurafenib, and sunitinib; sirolimus (rapamycin), everolimus and other mTOR inhibitors. Other examples include, but are not limited to, topoisomerase I inhibitors (e.g., irinotecan, topotecan, camptothecin and analogs or metabolites thereof, and doxorubicin); topoisomerase II inhibitors (e.g., etoposide, teniposide, and daunorubicin); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea). Moreover, exemplary chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and other inhibitors of proteins or enzymes known to be upregulated, over-expressed or activated in cancers, the inhibition of which downregulates cell replication.

The person skilled in the art would be aware that classification of the additional chemotherapeutic agent under one class (e.g. alkylating agent) does not exclude it from also be classified under another class.

Determining Clinical Response in a Subject

Methods for determining whether a subject has clinically responded to treatment will be known to persons skilled in the art. The term is broadly defined and may be determined for example by assessing treatment-related toxicity and response to treatment by various criteria such as the National Cancer Institute Common toxicity criteria (NCI-CTC) or response evaluation criteria in solid tumors (RECIST) criteria. Progression-free (PFS), and overall survival (OS) may also be assessed. The RESIST criterion uses computed tomography (CT) or magnetic resonance imaging (MRI) to measure the largest diameter of the targeted tumour or any de-novo appearance of new lesions.

In some examples, clinical response is determined according to the Gynaecological Cancer Intergroup (GCIG) CA125 response criteria. The GCIC measures serum levels of CA125. The biomarker CA125 is a glycoprotein produced and shed by some gynaecological tumours. Using a combination of GCIG and RECIST, patient responses can be categorised into complete response (CR), partial response (PR), stable disease (SD) and progressive disease (PD) (Rustin G J et al. (2011) PubMed PMID 21270624).

Methods of Treatment

The present disclosure also relates to methods for treating cancer (e.g. gynaecological cancer) in a subject in need thereof on the predicted likelihood of response. For example, the present disclosure provides methods for treating a subject who has been identified as responding positively to treatment with cyclophosphamide, or analogue or derivative thereof, based on expression of CCR4 on Teff cells of the subject. Therefore, in another aspect the present invention provides a method for treating cancer in a subject in need thereof comprising identifying a subject who will respond positively to treatment with cyclophosphamide, or an analogue or derivative thereof, according to a method described herein and treating the subject with cyclophosphamide, or an analogue or derivative or thereof.

The amount of cyclophosphamide or analogue or derivative thereof, administered to the subject will be at the discretion of the treating physician. For example, the amount of cyclophosphamide administered to the subject can be dependent on the subject being treated, on the subjects weight, the severity of the cancer, the manner of administration, and the treatment schedule. The amount and treatment schedule can be adjusted individually to provide levels of the active ingredients that are sufficient to maintain therapeutic or prophylactic effects.

In some examples, low dose cyclophosphamide is administered. In some examples, 50 mg cyclophosphamide is administered. In some examples, 100 mg or 150 mg of cyclophosphamide is administered.

In some examples, the cyclophosphamide is administered at least twice daily, at least daily, at least every second day, at least every three days, at least every four days, at least every 5 days, at least every 6 days, at least weekly, at least fortnightly, or at least monthly.

In some examples, administration is metronomic.

In some examples, the cyclophosphamide, or an analogue, derivative or active metabolite thereof, is administered orally or systemically.

In some examples, the cyclophosphamide, or an analogue, derivative or active metabolite thereof, is administered in a cyclical fashion. For example, the cyclophosphamide, or an analogue, derivative or active metabolite thereof, can be administered for a period of two days, three days, four days, five days, six days or seven days before administration is ceased for a period of time (for example, but not limited to, one, two, three of four weeks). The cycle can then be repeated at the treating physician's discretion. In one example, the cyclophosphamide, or an analogue, derivative or active metabolite thereof, is administered for three days followed by a rest period of X days (for example, 14 days). In one example, 50 mg of the cyclophosphamide, or an analogue, derivative or active metabolite thereof, is administered twice daily for three days followed by a rest period of X days (e.g. 14 days).

In some embodiments, the methods for treating may also comprise administering a therapeutic agent selected from the group consisting of chemotherapeutic agents, checkpoint inhibitors, vaccines and immunomodulatory agents. The person skilled in the art would be aware that classification of the therapeutic agent under one class (e.g. checkpoint inhibitor) does not exclude it from also being classified under a different class.

In some embodiments, the treatment methods may also comprise administering a non-drug based treatment. As used herein, "non-drug based" treatment includes, but is not limited to, radiation therapy or surgery or similar. For example, the tumour may be resected prior to the administration of the chemotherapeutic agent.

The frequently and type of treatment administered to the subject will be at the discretion of the treating physician.

Combination Therapies
Checkpoint Inhibitors

In some embodiments, the methods further comprise administering a checkpoint inhibitor. The checkpoint inhibitor can be administered to the subject either prior to, substantially simultaneously with, or after treatment with cyclophosphamide. In some embodiments, cyclophosphamide is administered prior to the checkpoint inhibitor. In some embodiments, the checkpoint inhibitor is administered prior to cyclophosphamide.

As used herein, "checkpoint inhibitors" include any agent that blocks or inhibits in a statistically significant manner, the inhibitory pathways of the immune system. For example, checkpoint inhibitors can affect Treg function. Checkpoint inhibitors include antibodies, or antigen binding fragments thereof, other binding proteins, biologic therapeutics or small molecules. In some embodiments, checkpoint inhibitors bind to and block or inhibit immune checkpoint receptors. In some embodiments, checkpoint inhibitors bind to and block or inhibit immune checkpoint receptor ligands. In some embodiments, checkpoint inhibitors may target for blocking or inhibition CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8+ (αβ) T cells), CD160 (also referred to as BY55), CGEN-15049, CHK 1 and CHK2 kinases, A2aR and various B-7 family ligands and a combination thereof. B7 family ligands include, but are not limited to, B7-1, B7-2, B7-DC, B7-H1, B7-H2, B7-H3, B7-H4, B7-H5, B7-H6 and B7-H7. In some embodiments, the checkpoint inhibitor interacts with a ligand of a checkpoint protein which may be CTLA-4, PDLI, PDL2, PDI, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. Checkpoint protein ligands include, but are not limited to, PD-LI, PD-L2, B7-H3, B7-H4, CD28, CD86 and TIM-3.

In some embodiments, the checkpoint inhibitor is a biologic therapeutic or a small molecule. In some embodiments, the checkpoint inhibitor is a monoclonal antibody, a humanized antibody, a fully human antibody, a fusion protein or a combination thereof. In some embodiments, checkpoint inhibitors include antibodies, or antigen binding fragments thereof, other binding proteins, biologic therapeutics or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Examples of checkpoint inhibitors include, but are not limited to, Tremelimumab (anti-CTLA-4 antibody), anti-OX40, PD-LI monoclonal Antibody (Anti-B7-HI; MEDI4736), MK-3475 (PD-1 blocker), Nivolumab (anti-PDI antibody), CT-011 (anti-PDI antibody), BY55 monoclonal antibody, AMP224 (anti-PDLI antibody), BMS-936559 (anti-PDLI antibody), MPLDL3280A (anti-PDLI antibody), MSB0010718C (anti-PDLI antibody) and Yervoy/ipilimumab (anti-CTLA-4 antibody).

Vaccines

In some embodiments, the methods further comprise administering a vaccine. The vaccine can be administered to the subject either prior to, substantially simultaneously with, or after treatment with cyclophosphamide. In some embodiments, cyclophosphamide is administered prior to the vaccine. In some embodiments, the vaccine is administered prior to cyclophosphamide.

Any suitable vaccine may be used. As used herein, vaccines include, but are not limited to, cancer vaccines. As used herein, a "cancer vaccine" refers to a vaccine which primes the immune system to attack cancer cells in the body. Accordingly, instead of preventing disease, a cancer vaccine stimulates the immune system (for example by inducing CD8 T cells and/or CD4 T cells) to attack a disease that already exists. In some embodiments, a cancer vaccine can use cancer cells, parts of cells, or pure antigens to increase the immune response against cancer cells that are already in the body. Non-limiting examples of cancer vaccines include tumour cell vaccines, antigen vaccines, dendritic cell vaccines, DNA or RNA vaccines, and vector based vaccines.

In some embodiments, the vaccine is an antigen vaccine comprising an antigen and an adjuvant and optionally a carrier. Examples of suitable adjuvants include Montanide ISO720, Alum etc. Antigen vaccines boost the immune system by using one or more antigens, in contrast to whole tumour cells that contain many thousands of antigens. These antigens can be peptides, proteins, mRNA or DNA. Antigen vaccines may be specific for a certain type of cancer because each tumour type may be identified by specific antigen profiles. In order to maximize the efficacy of these vaccines, it may be beneficial to combine multiple antigens in the vaccine depending on the antigen profile of a specific cancer.

In some embodiments, cancer vaccines can be made from actual cancer cells that have been removed from a subject. Once removed, the cancer cells are modified in the lab, typically with radiation, or via generation of a cancer cell lysate so they cannot form more cancer. The cancer cells can be further modified, for example, by adding chemicals or new genes, to make the cells more likely to be seen as foreign by the subject's immune system. The modified cells are then injected back into the subject. The immune system is able to recognize the antigens on these cells and through natural physiological processes seeks out and attacks/kills cells that express the intended antigen.

In some embodiments, the cancer vaccine comprises a dendritic cell vaccine. Dendritic cell vaccines are often autologous vaccines, and must often be made individually for each subject. The process used to create them is complex and expensive. For example, immune cells are removed from the blood of the subject and exposed to cancer cells or cancer antigens, as well as to other chemicals that turn them into dendritic cells and help them grow. The dendritic cells are then injected back into the subject, where they should provoke an immune response to cancer cells in the body.

In some embodiments, the cancer vaccine comprises a DNA and/or RNA vaccine.

Non-limiting examples of cancer vaccines include DCVax is Sipuleucel-T (or Provenge®). DCVax is a platform technology that uses activated dendritic cells and is designed to reinvigorate and educate the immune system to attack cancers. DCVax uses many active agents to hit many targets on the cancer (Liau, L M et al. Journal of Neurosurgery 90:1115-1124, 1999; Prins R M et al. J Immunother. 2013 February; 36(2):152-7). Sipuleucel-T is a dendritic cell vaccine that is used to treat advanced prostate cancer that is not treatable by traditional chemotherapeutic or hormone therapies. For this vaccine, the subject's own immune cells are isolated from the subject and the immune cells are then exposed to chemicals to convert them into dendritic cells. The dendritic cells are exposed to prostatic acid phosphatase (PAP) which, when reintroduced into the subject, produces an immune response against prostate cancer.

Immunomodulatory Agents

In some embodiments, the methods further comprise administering an immunomodulatory agent. The immunomodulatory agent can be administered to the subject either prior to, substantially simultaneously with, or after treatment with cyclophosphamide. In some embodiments, cyclophosphamide is administered prior to the immunomodulatory agent. In some embodiments, the immunomodulatory agent is administered prior to cyclophosphamide.

As used herein, an "immunomodulatory agent" includes a compound that induces or increases immunogenicity and immune recognition of cancer cells by the host's immune system. For example, the immunomodulatory agent can be an immunomodulating antibody, cancer vaccine, therapeutic cytokine, cellular therapy or combinations thereof. In some embodiments, the immunomodulating antibody is selected from the group consisting of anti-CTLA-4, an anti-PDL1, an anti-PDL2, an anti-PD1, an anti-CD137, an anti-CD40 or an anti-OX-40 antibody. In some embodiments, the cancer vaccine is as defined herein. For example, the cancer vaccine can be selected from the group consisting of anti-idiotypic antibodies, inhibitors of angiogenesis, Tumor Antigen specific peptides or recombinant proteins. In some embodiments, the cellular therapy is selected from the group consisting of T cells, stem cells, dendritic cells, gene- or pharmacologically-modified immune and/or cancer cells.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

EXAMPLES

Methods 1.1 Trial Design and Patient Details

Ten (10) human patients with gynaecological cancers with ages ranging from 62-82 years were recruited in a bicentric phase II trial. The patients had advanced treatment-refractory gynaecological tumours and were recruited from the Royal Women's Hospital, Melbourne, Australia (n=3) and the University Hospital Leuven, Belgium (n=7) see Table 1. Disease progression was determined using RECIST and GCIG CA125 criteria (Rustin G J et al., (2011) Official journal of the International Gynaecological Cancer Society February; 21(2):419-23). From the time of recruitment, written consent was obtained from patients and pre-treatment blood samples were collected. Patients received oral doses of 50 mg cyclophosphamide twice daily (morning and evening), for 3 consecutive days and blood was collected 2 weeks later in EDTA coated tubes for whole blood and serum separation tubes for sera (BD Vacutainer, BD, USA). The treatment cycle and blood sampling were repeated at fortnightly intervals for up to 8 cycles. For healthy samples, buffy coats were obtained from routine blood donations, acquired at the Australian Red Cross Blood Service.

TABLE 1

Patient summary

| Patient ID | Age | Tumour type | Prior Treatment | Disease status at inclusion | Disease outcome | Cycles of treatment |
|---|---|---|---|---|---|---|
| Pt 1 | 70 | Papillary serous cystadenocarcinoma | Surgery, 2 lines chemo, | Progessive disease (PD) with rising CA125 | PD | 1 |
| Pt 2 | 79 | Papillary serous cystadenocarcinoma | Surgery, 2 lines chemo, | PD - with progressive nodal abnormalities above and below diaphragm and new peritoneal abdo/pelvic disease | PD | 2 |
| Pt 3 | 69 | Papillary serous cystadenocarcinoma | Surgery, 2 lines chemo, | PD with short bowel syndrome | PD | 5 |

TABLE 1-continued

Patient summary

| Patient ID | Age | Tumour type | Prior Treatment | Disease status at inclusion | Disease outcome | Cycles of treatment |
|---|---|---|---|---|---|---|
| Pt 4 | 74 | Ovarian carcinoma | Surgery, 3 lines chemo | PD with newly formed hepatic lesion, hepatogastric, lymphnode, peritoneal and mesenteric lesions present | PD | 2 |
| Pt 5 | 80 | Ovarian carcinoma | Surgery, 3 lines chemo, provera | PD with increase of peritoneal metastases with ascites formation | PD | 2 |
| Pt 6 | 73 | Ovarian carcinoma | 3x surgery, 4 lines chemo | PD with increase and new formation of abdominal metastases and possible lymph node metastases | SD | 3 |
| Pt 7 | 64 | Peritoneal tumour | Surgery, 6 lines chemo, avastin | PD with peritoneal, omental, vertebral, hepatic and possible gastric metastases | PD | 2 |
| Pt 8 | 62 | Endometrial carcinoma | 2x surgery, 1 line chemo, radiotherapy | PD with increase of hepatic, brain and possible renal metastases | SD | 8 |
| Pt 9 | 74 | Malignant mixed Müllerian tumour (MMMT) | Surgery, 1 line chemo | PD with increase of known retroperitoneal lesions and occurrence of a new lesion | SD | 5 |
| Pt 10 | 82 | Ovarian carcinoma | 2x surgery, 5 lines chemo, provera | PD with increase of LN metastases in upper abdomen, metastases in mediastinum and formation of lung metastases | PD | 2 |

1.2 Isolating Peripheral Blood Mononuclear Cells

Peripheral blood mononuclear cells (PBMCs) were isolated within 24 hours of blood collection via Ficoll (Amersham Pharmacia Biotech, Sweden) density gradient centrifugation. Cells were then washed in Dulbecco's Phosphate Buffered Saline (dPBS, Sigma-Aldrich, USA). The isolated PBMCs were frozen down in a freeze medium containing 10% DMSO (Sigma-Aldrich, USA) and 90% heat-inactivated fetal calf serum (GIBCO, Life Technologies, USA) or 90% human AB serum (Sera Laboratories International, UK) at a speed of 1° C./min at −80° C. and subsequently stored in liquid nitrogen. Upon thawing, each vial of frozen PBMCs was quickly defrosted in a 37° C. water-bath and re-suspended in AIM-V media (Life Technologies, USA) with 5% normal human serum (HS, Sigma-Aldrich, USA) (complete AIM-V media).

1.3 Counting Cells

Cells were counted using a glass haemocytometer (Hausser Scientific, USA) on an inverted microscope (Leica Microsystems, Germany). Cells were diluted in Trypan Blue stain (GIBCO, Life Technologies, USA) to determine cell viability.

Formula for calculating cell count:

Total cells=cell count×dilution factor×volume of cells in the tube×$10^4$.

1.4 Serum CCL22 Detection

The concentrations of CCL22 in sera from cancer patients and healthy donors were determined using a Multiplex Bead Immunoassay Kit (human chemokine 5-plex panel, Life Technologies, USA) following the manufacturer's instructions. Samples were acquired on a Bio-Plex 200 system (Bio-Rad, USA), collecting a minimum of 100 events. Results were analysed using the Bio-Plex Manager version 5 software (Bio-Rad, USA).

1.5 Flow Cytometric Analysis

To determine the frequency and phenotype of T cell populations in PBMCs, multicolour flow cytometry was performed using the following surface antibodies: anti-CD3, anti-CD8, anti-CD4, anti-CD25, and anti-CCR4. Antibodies were diluted in dPBS with 5% HS (staining buffer). Cells were stained at room temperature for 15 mins at a final concentration of $10^7$ cells/150 µl of antibody cocktail. Cells were then washed twice with stain buffer. A fixable dead cell dye (live/dead, fixable aqua dead cell stain kit, Life Technologies, USA) was used to distinguish between dead and live cells. The dye was diluted 1/500 in staining buffer and cells incubated for 15 mins at room temperature at a final concentration of $10^7$ cells/150 µl of diluted dye and then washed twice in stain buffer. Intracellular levels of FoxP3 were determined following fixation and permeabilisation of cells using a fixation/permeabilisation buffer kit (eBioscience, USA). The fixation/permeabilisation concentrate was diluted 1:3 with the diluent. Cells were then resuspended in 50 µl of the diluted fixation/permeabilisation solution for 30 mins at 4° C. Intracellular anti-FoxP3 and anti-Ki67 were diluted in fixation/permeabilisation wash buffer (eBioscience, USA). Cells were washed in fixation/permeabilisation wash buffer then resuspended in the diluted intracellular antibodies at a final concentration of $10^7$ cells/150 µl and incubated for 15 mins at room temperature. Cells were then washed twice and resuspended in dPBS with 1% paraformaldehyde (PFA, Sigma-Aldrich, USA). Flow cytometry data were acquired on a Becton Dickinson LSR II flow cytometer using FACSDiva software, acquiring a minimum of 100,000 events per sample. Fluorescence minus one (FMO) controls and isotype-matched antibodies were also used to enable accurate gating. Data were analysed using Flowjo software (TreeStar, USA). The list of antibodies is shown in Table 2.

1.6 T Cell Cytotoxicity Assay

The cytotoxic capacity of T cells was determined by culturing PBMCs with complete AIM-V media at $10^6$ cells/500 µl/well in a 48 well plate. Cells were then stimulated for 6 hours with 50 ng/ml of phorbol 12-myristrate 13-acetate (PMA, Sigma-Aldrich, USA) and 1 µg/ml of ionomycin (Sigma-Aldrich, USA) in the presence of protein transport inhibitor (1/1500 dilution of stock, BD GolgiStop, BD biosciences, USA) and anti-CD107a (1/20 dilution of stock, BD Pharmingen, USA) at 37° C. in a 5% $CO_2$ humidified incubator. Brefeldin A (eBioscience, USA) was added at 3 µg/ml for the last 4 hours of incubation. After incubation, cells were washed and labelled for surface markers as described above. Cells were analysed using flow cytometry, unstimulated cells, fluorescence minus one (FMO) and isotype matched antibodies were also used as controls. Data were collected and analysed as above.

1.7 In Vitro Drug Experiment

To investigate the effect of cyclophosphamide on T cells in vitro, PBMCs from patients, pre-treatment and healthy donors were treated with mafosfamide (Niomech, Germany), an analogue of the pharmacologically active liver metabolite of cyclophosphamide. Mafosfamide was reconstituted upon use at a concentration of 80 mg/ml in sterile Milli Q water. CD4+ and CD8+ T cells were purified by labelling cells with the respective antibodies as described above, then using fluorescence activated cell sorting. Whole PBMCs or purified CD4+ and CD8+ T cells were cultured in complete AIM-V media at $3 \times 10^5$ cells/150 µl/well in a 96 well plate with either mafosfamide at 1.5 µg/ml or media for 72 hours at 37° C. in a 5% $CO_2$ humidified incubator. For purified cell cultures, IL-2 was added at a concentration of 20 units/ml to sustain cell viability. Following incubation, cells were washed and CCR4 expression on Tregs and effector T cells were determined using flow cytometry as described above. To determine the cytokine secretion profile of T cells following in vitro treatment, cells were treated with mafosfamide as described above at a time course of 24, 48 and 72 hours. Cells were stimulated with PMA and ionomycin as described above in the last 6 hours of incubation for each time point. Cells were then washed and labelled for surface markers and then intracellular cytokine staining as described above using anti-IL-4 (BD Pharmingen, USA) and anti-IL-2 (BD Pharmingen, USA).

1.8 Histone 3 Acetylation Detection

The acetylation of histone 3 at lysine (H3K)9, H3K14 and H3K18 was assessed using flow cytometry. Initially cells were cultured as described above in mafosfamide at 1.5 µg/ml or IL-4 (R&D systems, USA) at 10 ng/ml or with IL-2 (R&D systems, USA) at 20 units/ml for 72 hours. In the last 4 hours of culture, 50 nM panobinostat (LBH589, a pan histone deacetylase (HDAC) inhibitor was added to the IL-2 cultures. Cells were harvested and prepared for flow cytometry analysis as described above. Following surface labelling, fixation and permeabilisation, cells were labelled with unconjugated anti-H3K9, anti-H3K14 and anti-H3K18 (Cell Signalling Technology, USA). Secondary labelling was performed using an Alexa Fluor 488 conjugated donkey anti-rabbit Ig antibody (Biolegend, USA). Data were collected and analysed as above.

1.9 Migration Assay

PBMCs from healthy donors were treated with mafosfamide as described above. Following 72 hours of incubation, cells were washed and viable cells seeded into 24 well transwell inserts (Corning, USA) at $2.5 \times 10^5$ cells/100 µl/insert in AIM-V media with 0.5% bovine serum albumin (BSA, Sigma-Aldrich, USA). Either 600 µl of CCL22 (R&D Systems, USA) at 100 ng/ml in AIM-V media or AIM-V media alone were added to each well beneath the transwell insert. Cells were incubated at 37° C. in a 5% $CO_2$ humidified incubator for 2 hours, following which, they were counted and T cell subsets determined using flow cytometry. Migration indices were calculated by dividing the percentage of cells that migrated towards CCL22 by that of cells that migrated towards media alone.

1.10 Statistics

To determine statistical significance, non-parametric tests were used. To compare differences in patients between in vitro and in vivo post-treatment and pre-treatment samples, Wilcoxon matched-pairs signed rank tests were performed while Mann-Whitney tests were used to compare between patient groups or between patients and healthy donors. To determine significance in fold changes following treatment, Wilcoxon signed rank tests were performed to test the null hypothesis that the means were equal to 1. Spearman correlation tests were used to determine correlations between parameters. Statistical analyses were performed using GraphPad Prism (v.6, GraphPad Software, Inc, USA). $p < 0.05$ was considered significant. Mean values were presented±the standard error of the mean (SEM).

TABLE 2

List of antibodies

| Antibody | Fluorochrome | Company (catalogue number) |
| --- | --- | --- |
| CD3 | Q655 | Life Technologies (Q10012) |
| CD3 | BV655 | Biolegend (317324) |
| CD3 | V450 | BD Horizon (560365) |
| CD4 | AF700 | BD Pharmingen (557922) |
| CD4 | APC-CY7 | BD Pharmingen (557871) |
| CD8 | Q605 | Life Technologies (Q10009) |
| CD8 | BV605 | Biolegend (301039) |
| CD8 | Percp-Cy5.5 | BD Pharmingen (560662) |
| CD25 | PE | BD Pharmingen (555432) |
| CD25 | PE-CF594 | BD Pharmingen (562403) |
| FoxP3 | AF700 | eBioscience (56-4776-41) |
| FoxP3 | Percp | eBioscience (45-4776-73) |
| FoxP3 | APC | eBioscience (17-4776-42) |
| FoxP3 | eFluor 450 | eBioscience (48-4776-42) |
| CCR4 | PE-Cy7 | BD Pharmingen (557869) |
| CCR4 | PE | BD Pharmingen (551120) |
| Ki67 | V450 | BD Horizon (561281) |
| IL-2 | APC | BD Pharmingen (554567) |
| IL-4 | Percp-Cy5.5 | BD Pharmingen (561234) |
| CD107a | Biotin | BD Pharmingen (555799) |
| CD107a | PE | BD Pharmingen (555801) |
| H3K9 | unconjugated | Cell Signalling (9649) |
| H3K14 | unconjugated | Cell Signalling (7627) |
| H3K15 | unconjugated | Cell Signalling (13998) |
| Streptavidin | APC-efluor 780 | eBioscience (47-4317-82) |
| CD3 | Purified | Biolegend (317315) |
| CD28 | Purified | BD Pharmingen (556620) |
| IL-6 | Purified | R & D Systems (MAB2062) |

Example 1

An Increase in CCR4+ T Cells Following Treatment is Associated with Increased Survival in Patients with Gynaecological Malignancies To investigate the effect of cyclophosphamide on CCR4 expression within T cells, the frequency of CCR4+ cells pre-treatment (n=mean of 7-8 time points) was compared to the frequencies following each cycle of treatment (n=mean of 3-6 time points) for each individual patient. Of the 10 patients, 4 had significant increases in the frequency of CCR4+ cells within CD3+ T cells (increased % CCR4 or CCR4 spike, FIG. 2A), following at least one cycle of treatment and this occurred within the first 3 cycles of treatment, while in the other 6 patients, the frequency of CCR4+ cells within CD3+ T cells remained relatively constant (constant % CCR4+ or CCR4 steady, FIG. 2 and Table 3).

TABLE 3

Change in % CCR4 expression following cyclophosphamide treatment

| Patient ID | Pre-treatment | Cycle 1 | Cycle 2 | Cycle 3 | Cycle 4 | Cycle 5 |
|---|---|---|---|---|---|---|
| pt1 | 13.4 | 20.3 | | | | |
| pt2 | 13.9 | 13.3 | | | | |
| pt3 | 30.9 | 32.2 | 26.1 | | 34.5 | 22.6 |
| pt4 | 15.4 | 13.6 | 14.4 | | | |
| pt5 | 11.6 | 9.5 | 13.4 | | | |
| pt6 | 18.4 | 16.4 | 14.9 | 58.8*** | | |
| pt7 | 23.4 | 20.1 | | | | |
| pt8 | 22.0 | 55.5*** | 33.0 | 11.6 | 10.6 | 10.6 |
| pt9 | 10.2 | 52.3*** | 77.2*** | 9.9 | 6.1 | 7.0 |
| pt10 | 11.5 | 42.4*** | 60.1*** | | | |

***significantly different compared to pre-treatment p < 0.001

The 'CCR4 spike' patients survived significantly longer (approximately 3 times longer) than CCR4 steady patients with a mean overall survival of nearly a year more, 476±80 days compared to 163±37 days (p<0.01). The timing of disease stabilization coincided exactly with the time of their individual spike in CCR4+ T cells (not shown). None of the 6 patients with 'CCR4 steady' cells following treatment achieved stable disease (shown in FIG. 2B). Of the 4 CCR4 spike patients, 3 additionally achieved stable disease and intriguingly, disease stabilization coincided completely with the time of their CCR4+ T cells increase (FIG. 2C). None of the 6 patients with unchanged constant % CCR4 cells (CCR4 steady) following treatment achieved disease stability (FIG. 2C).

Example 2

Figure 3:
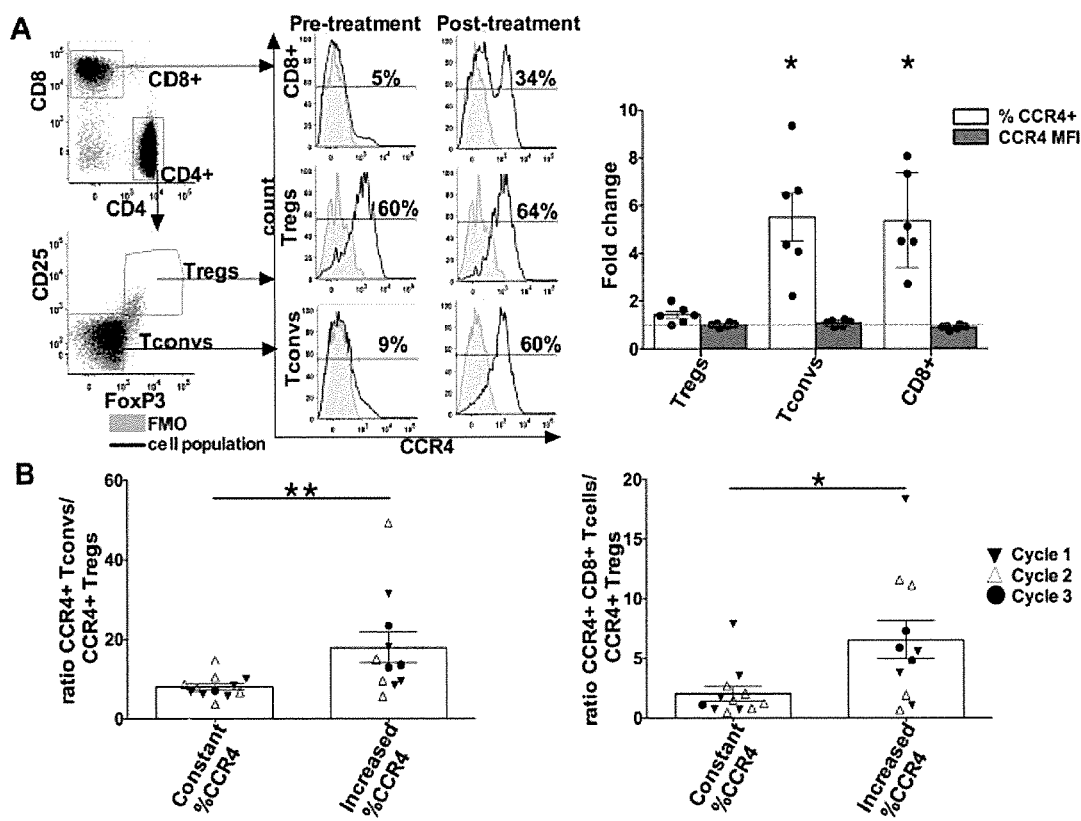
FIG. 3. CCR4 expression is upregulated on effector T cell populations. An analysis was restricted to FoxP3+CD25+CD4+ T cells (Tregs), FoxP3−CD25−CD4+ T cells (Tconvs) and CD8+ T cell in the increased % CCR4 patients at the time-points where there was a significant increase in the frequency of CCR4+ T cells (n=6 from 4 patients). Fold increases, from pre-treatment levels, in these frequencies of CCR4+ cells along with fold increases in the mean fluorescence intensity (MFI) of CCR4 were plotted. *$p<0.05$, statistical significance in fold change from pre-treatment levels. B the ratios of Tconvs to Tregs and CD8+ T cells to Tregs were calculated for the first 3 cycles of treatment for all patients. These ratios were then compared between constant % CCR4 (n=12 from 6 patients) patients and for increased % CCR4 patients (n=11 from 4 patients). * represents $p<0.05$ and ** represents $p<0.01$ statistical significance between patient groups and graphs show means±standard error of the mean (SEM).

CCR4 Expression is Increased on CD8+ T Cells and Effector T Cells but not Treg Low dose cyclophosphamide treatment resulted in a transient increase in the frequency of CCR4+ cells within CD3+ T cells in a subgroup of patients. To further determine the specific T cell subsets that were expressing CCR4, the inventors focused their analysis to these patients at the time points where an increase in the frequency of CCR4+ cells within CD3+ T cells was observed. T cells were then divided into regulatory T cell, FoxP3+CD25+CD4+ (Tregs) and effector T cell subsets that were FoxP3−CD25−CD4+ (Tconvs) or CD8+ T cells (FIG. 3A). The frequencies of CCR4+ cells within the respective subsets were determined and post-treatment values normalised to pre-treatment values. The increase in the frequency of CCR4+ cells within CD3+ T cells was driven by an increase in CCR4 expression on the effector T cell populations as both Tconvs and CD8+ T cells showed a significant 5 fold increase in the frequency of CCR4+ cells (p<0.05 in both cases) compared to pre-treatment levels (FIG. 3A). The frequency of CCR4+ cells within Tregs was not significantly increased (FIG. 3A). The fold changes in CCR4 mean fluorescence intensity (MFI) within Tregs, Tconvs and CD8+ T cells were also assessed relative to pre-treatment levels and in all 3 populations CCR4 MFI remained unchanged (FIG. 3A).

The ratio of effector T cells to Tregs within the tumour microenvironment is a well-established parameter that is associated with clinical outcome in gynaecological cancer patients (Gooden M J et al., (2011) British journal of Cancer 28; 105(1):93-103). The inventors compared the pooled ratios of CCR4+ Tconvs and CCR4+ CD8+ T cells to CCR4+ Tregs within the first 3 cycles of treatment between increased % CCR4 patients and constant % CCR4 patients. Increased % CCR4 patients had an over 2 fold higher mean ratio of Tconvs to Tregs (p<0.01) and over 3 fold higher mean ratio of CD8+ T cell to Tregs (p<0.05) compared to constant % CCR4 patients (FIG. 3B).

Figure 4:
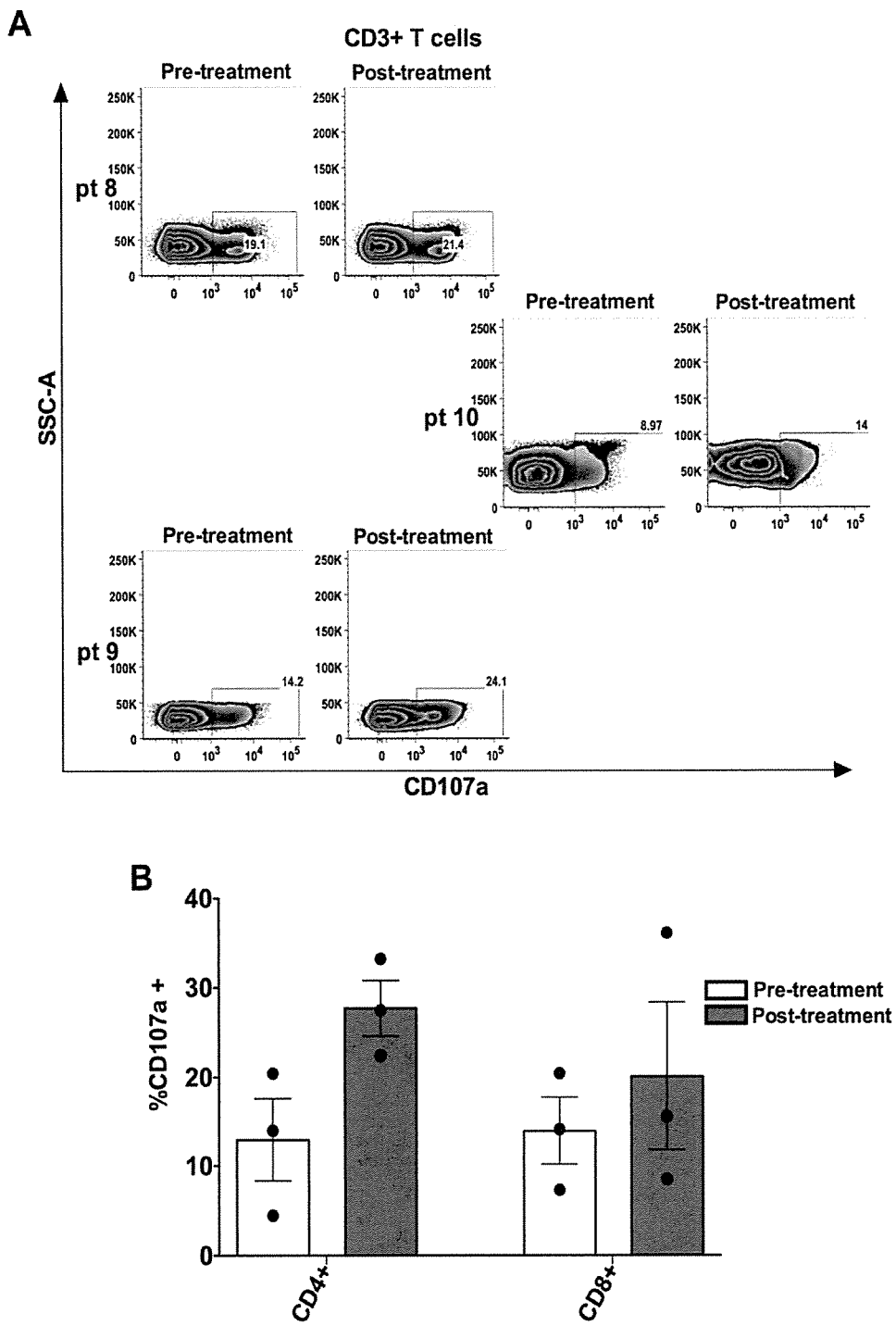
FIG. 4. Following up-regulation of CCR4 expression, T cells retain their cytotoxicity. The cytotoxic function of T cells from increased % CCR4+ T cells patients was assessed at time-points where there was a significant increase in the frequency of CCR4+ T cells. PBMCs were stimulated for 6 hours with 50 ng/ml of Phorbol 12-myristrate 13-acetate (PMA) and 1 μg/ml of ionomycin in the presence of protein transport inhibitor and anti-CD107a. A and B, The expression of CD107a on CD4+ and CD8+ T cells was then determined by flow cytometry and compared to pre-treatment levels (n=3 patients). Graphs show means±standard error of the mean (SEM).

CCR4 expression on T cells is associated with a loss of cytotoxicity (Kondo T et al. (2009) International Immunology 21(5):523-32). The inventors therefore determined whether cytotoxic function of CD4+ or CD8+ T cells was affected by the increase in CCR4+ cells within these populations. The frequencies of CD107a+ cells within CD4+ and CD8+ T cells were determined using samples from 3 of the 4 increased % CCR4 patients at one of the time points when CCR4+ T cell frequencies was increased. The mean frequency of CD107a+ cells in both CD4+ and CD8+ populations was increased compared to pre-treatment samples, however neither increase was significant (FIGS. 4A and B).

Example 3

The Patients with Increased Ability to Generate CCR4+ Effector CD4 T Cells In Vitro by Mafosfamide Pre-Treatment, Respond In Vivo to Cyclophosphamide with a "CCR4 Spike"

Figure 5:
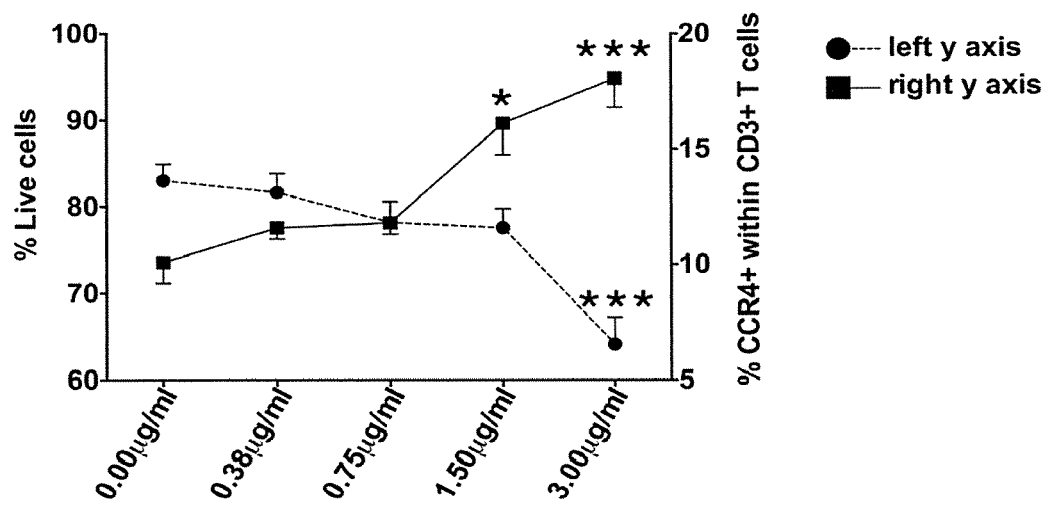
FIG. 5 Optimal dose of mafosfamide. Healthy donor PBMCs were treated with varying concentrations of mafosfamide as described above. The frequencies of CCR4+ T cells (right y axis) and live cells were (left y axis) determined using flow cytometry (n=6 donors). * represents $p<0.05$ and *** represents $p<0.001$ statistical significance compared to untreated. Graphs show means±standard error of the mean (SEM).

To determine whether in the increase in the frequency of CCR4+ T cells was directly due to cyclophosphamide, peripheral blood mononuclear cells (PBMC) from patients pre-treatment, and from healthy donors were cultured with mafosfamide, the bioactive isoform of cyclophosphamide. A titration determined the optimal non-toxic mafosfamide dose to be 1.5 µg/ml (FIG. 5). Healthy donor along with patient pre-treatment PBMCs were cultured for 3 days with 1.5 µg/ml of mafosfamide or media alone. Mafosfamide treated PBMCs from both healthy donors and patients had a significantly higher frequency of CCR4+ cells within CD3+ T cells compared to the media (healthy: 22.9%±1.79% compared to 15.4%±1.47% p<0.001 and Cancer: 24.4%±3.14% compared to 19.6%±2.82%, p<0.01, FIG. 6A).

Similar to the in vivo observation, when the fold changes in the frequency of CCR4+ cells were determined for Tregs, Tconvs and CD8+ T cells, relative to the media, mafosfamide treated PBMCs had significant increases in the frequency of CCR4+ cells within Tconvs (Healthy: 1.45 fold, p<0.05 and Cancer: 1.18 fold, p<0.05) and CD8+ T cells (Healthy: 2.52 fold, p<0.05 Cancer: 1.61 fold, p<0.05). No significant changes were observed in the frequencies of CCR4+ cells within Tregs (FIG. 6B). This trend was similar between healthy donors and cancer patients, however the fold increases in CCR4+ T cells within Tconvs (p<0.01) and CD8+ T cells (p<0.01) were higher in healthy donors than in cancer patients (FIG. 6B). Mafosfamide treatment did not alter the MFI of CCR4 on any of the cell populations in both healthy donors and cancer patients (FIG. 6B).

Also similar to the in vivo observations, the differential control in CCR4 expression by mafosfamide between effector and regulatory T cell populations resulted in an over 2 fold significant increase in the mean ratios of CCR4+ CD4+ Tconvs to CCR4+ Tregs (p<0.05) and CCR4+ CD8+ T cells to CCR4+ Tregs (p<0.05) compared to untreated cells for both healthy donors and cancer patients (FIG. 6C).

A comparison of the upregulation in frequency of CCR4+ CD4 T cell effectors between CCR4 steady patients (n=6) and CCR4 spike patients (n=4) patients (p<0.0005), represented as fold increase, is shown in FIG. 6D.

Figure 8:
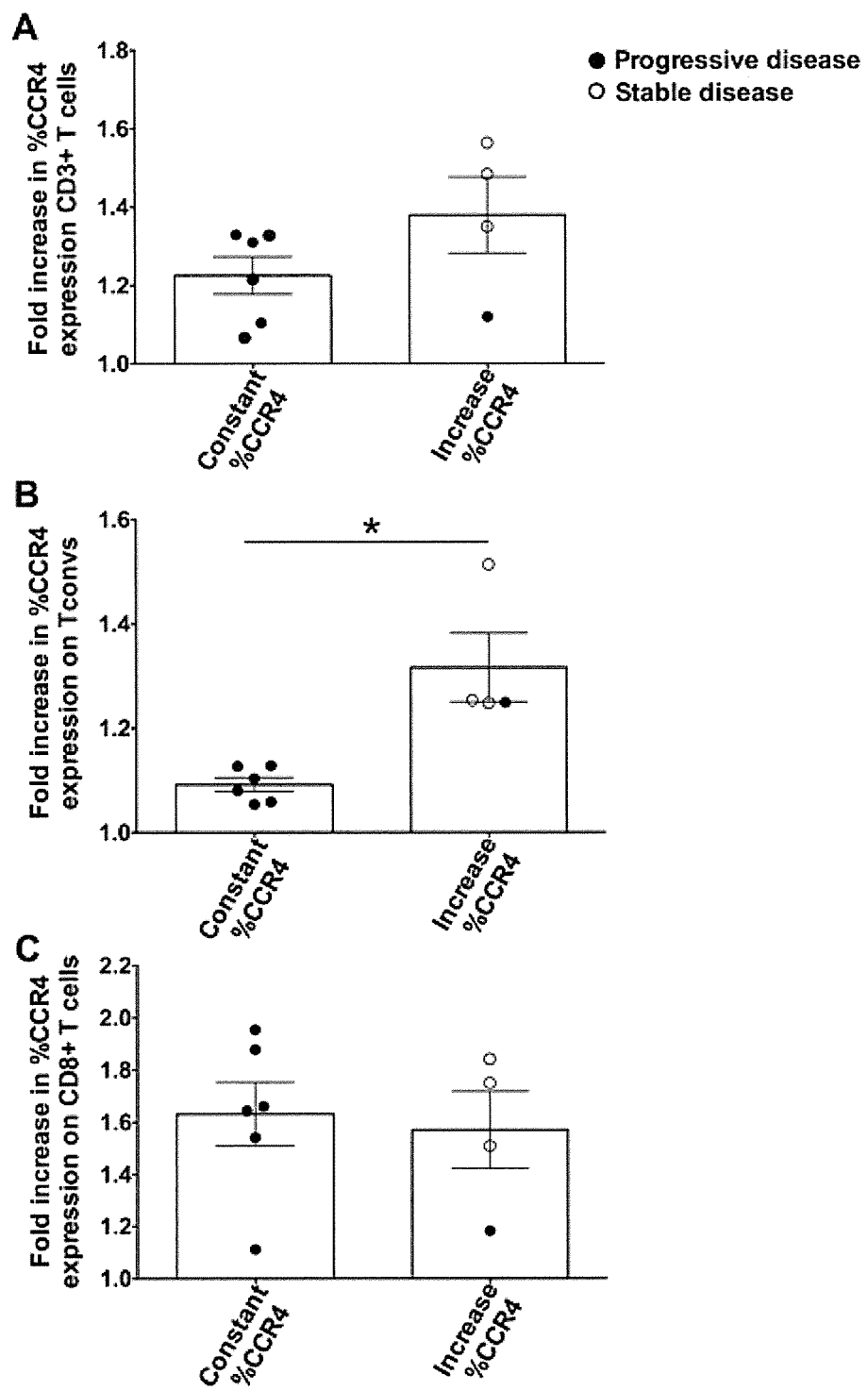
FIG. 8 A comparison of the up-regulation in the frequency of CCR4+ T cells between constant % CCR4 patients and increase % CCR4 patients. (A), (B) and (C), the fold changes in CCR4 expression on CD3+ T cells, Tconvs and CD8+ T cells in cancer patient pre-treatment samples, following in vitro treatment with mafosfamide were compared between constant % CCR4 patients (n=6 patients) and increase % CCR4 patients (n=4 patients). * represents $p<0.05$ statistical significance between patient groups. Graphs show means±standard error of the mean (SEM).

The inventors further investigated whether increased % CCR4 patients differentiated themselves from constant % CCR4 patients in their response to mafosfamide, as this may have been indicative of a response bias pre-treatment. However, while the fold increase in the frequency of CCR4+ cells within CD3+ T cells was slightly higher for increased % CCR4 patients compared to constant % CCR4 patients, this difference was not statistically significant (FIG. 8A). When the fold change in CCR4+ cells within Tconvs and CD8+ T cells were compared between increased % CCR4 patients and constant % CCR4 patients, the fold increase within Tconvs was significantly higher in increased % CCR4 patients compared to constant % CCR4 patients (1.32 compared to 1.09, p<0.05, FIGS. 8B and C).

Example 4

Figure 7:
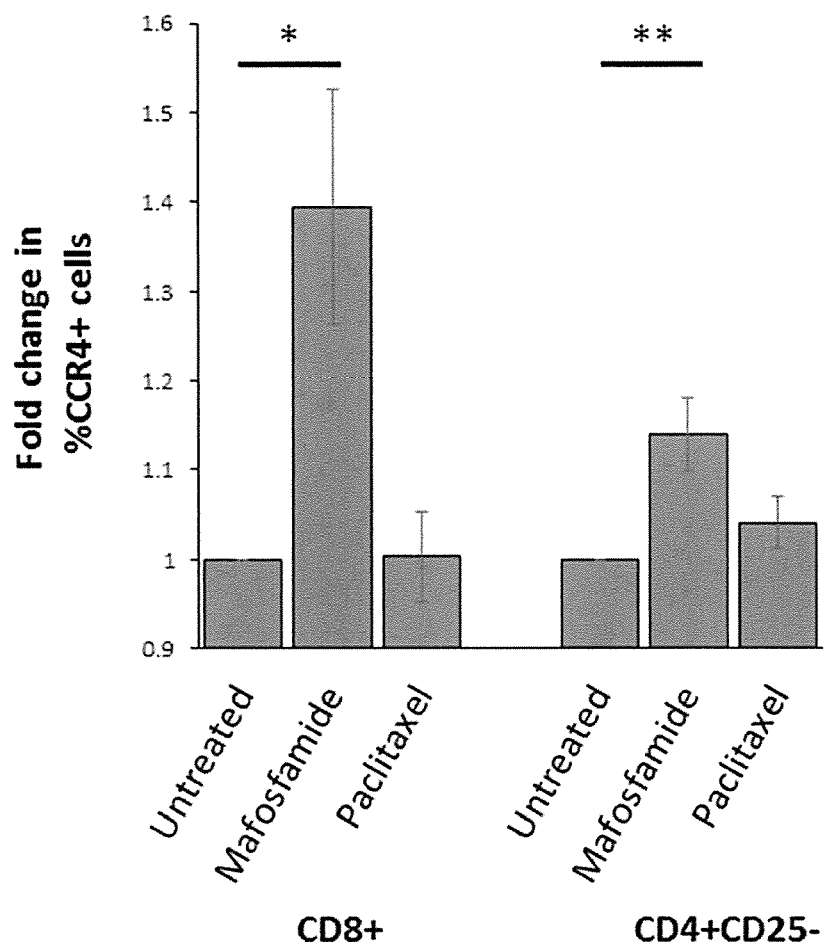
FIG. 7 Paclitaxel (a antineoplastic agent) does not induce the expression of CCR4 on T cells. Healthy donor PBMCs were cultured with media alone, 1.5 μg/ml of mafosfamide or 30 ng/ml of paclitaxel for 72 hours at 37° C. in a 5% $CO_2$ humidified incubator. The expression of CCR4 on CD8+ and CD4+CD25− T cells was then determined using flow cytometry and the % CCR4 expression normalised to media alone (n=8). * represents $p<0.05$ and ** represents $p<0.01$ statistical significance between treated and media alone cells. Graph shows means±standard error of the mean (SEM).

Paclitaxel does not Significantly Increase the Frequency of CCR4+ T Cells in Healthy PMBCs To determine whether in the increase in the frequency of CCR4+ T cells occurred upon treatment with paclitaxel (another antineoplastic agent), peripheral blood mononuclear cells (PBMC) from healthy patients were cultured with mafosfamide and paclitaxel. Healthy donor PBMCs were either incubated in media alone, 1.5 µg/ml of the active metabolite of cyclophosphamide mafosfamide or 30 ng/ml of Paclitaxel for 72 hours at 37° C. in a 5% $CO_2$ humidified incubator. Cells were harvested and flow cytometry analysis used to determine CCR4 expression on CD8+ and CD4+ CD25− T cells. Mafosfamide treated CD8+ and CD4+ CD25− T cells from healthy donors had a significantly higher fold increase of CCR4+ cells relative to untreated cells compared to paclitaxel treated cells, (CD8+: 1.39 compared to 1.00 p<0.05 and CD4+CD25−: 1.14 compared to 1.04, p<0.01, FIG. 7).

Example 5

Mechanism of Induction of CCR4 Expression on T Cells

Figure 9:
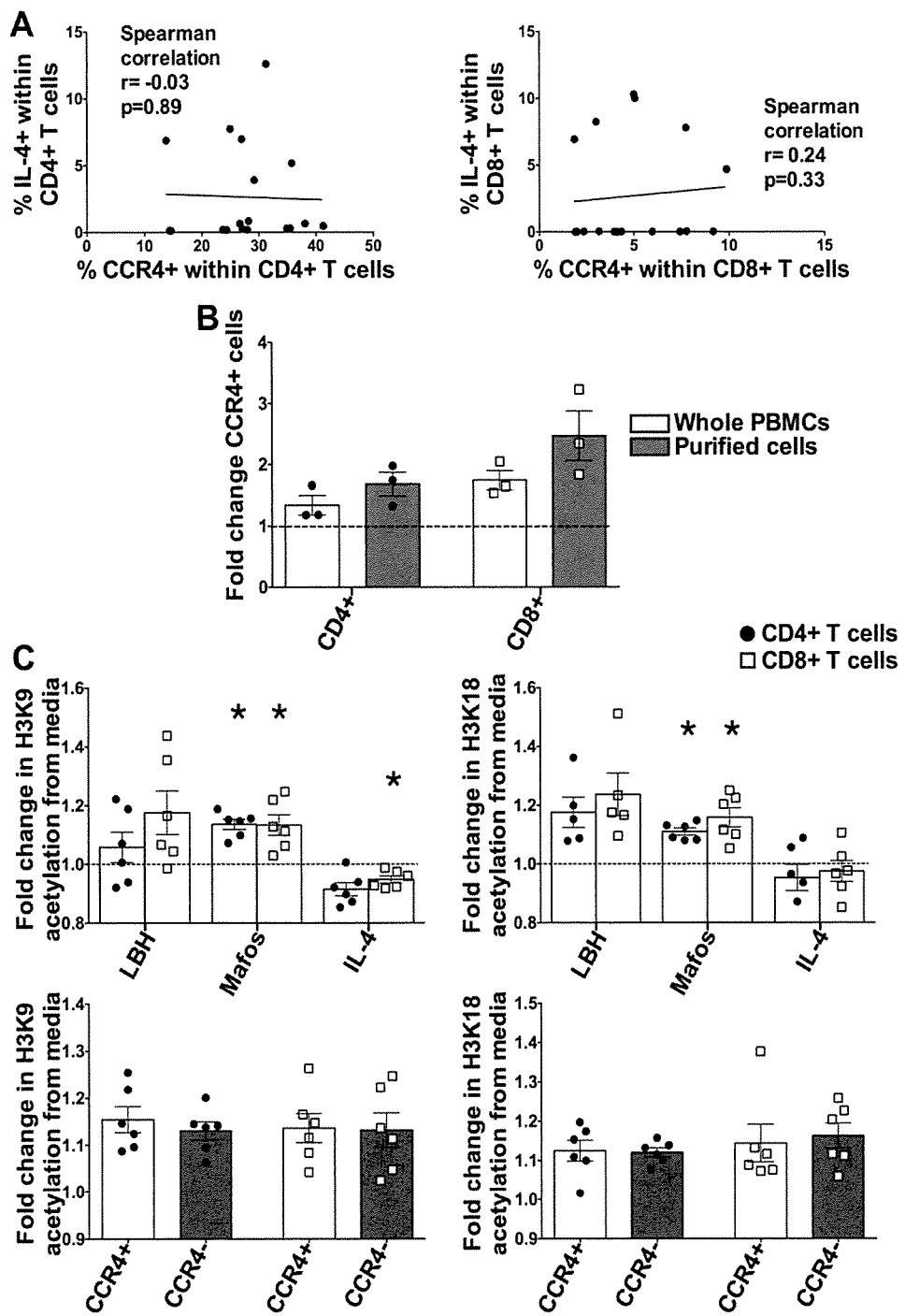
FIG. 9 The mechanism of CCR4 induction by mafosfamide. Healthy donor PBMCs were cultured with or without 1.5 μg/ml of mafosfamide for 24, 48 and 72 hours. In the last 6 hours of incubation, cells were stimulated with 50 ng/ml of Phorbol 12-myristrate 13-acetate (PMA) and 1 μg/ml of ionomycin. Brefaldin A was added at 3 μg/ml for the last 4 hours of incubation. A the frequency of IL-4+ cells was determined using flow cytometry and correlated with the corresponding frequencies of CCR4+ T cells in unstimulated cells using spearman correlation analysis (n=18 points from 6 donors). B CD4+ and CD8+ T cells were purified using fluorescence activated cell sorting and then cultured in with or without 1.5 μg/ml of mafosfamide in the presence of 20 units/ml of IL-2 for 72 hours. The frequency of CCR4+ cells was then determined using flow cytometry and fold changes from untreated samples calculated. The fold changes in the frequency of CCR4+ T cells were compared between purified T cells from and T cells from cultures of whole PBMCs (n=3 donors). C PBMCs were cultured with either mafosfamide (mafos) at 1.5 μg/ml or IL-4 at 10 ng/ml or IL-2 at 20 units/ml for 72 hours. In the last 4 hours of incubation 50 nM LBH589 was added to the IL-2 cultures. The intracellular levels of acetylation of H3K9, H3K14 and H3K18 were determined using flow cytometry (n=6 donors). The MFI of acetylation of H3K9, H3K14 and H3K18 were calculated and normalised to untreated levels for CD4+ and CD8+ T cells and for CCR4+ and CCR4− cells within them. * represents p<0.05 statistical significance in fold change from untreated levels. Graphs show means±standard error of the mean (SEM).
Figure 10:
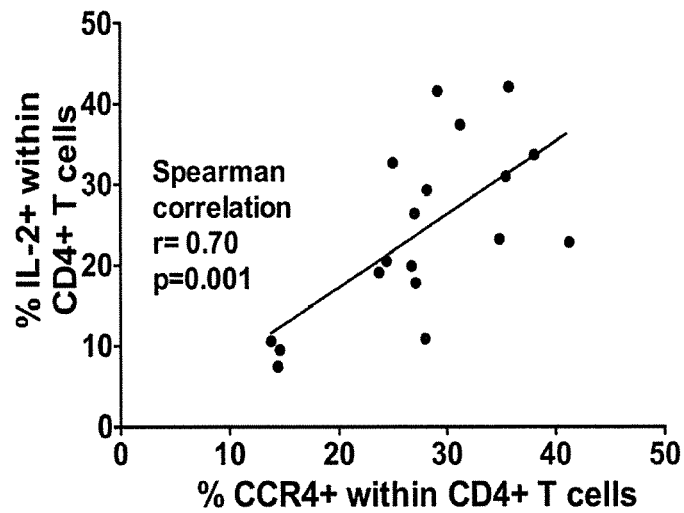
FIG. 10 Mechanism of CCR4 induction. Healthy donor PBMCs were cultured with or without 1.5 μg/ml of mafosfamide for 24, 48 and 72 hour. Cells were then stimulated for intracellular cytokine analysis as described above. A and B the frequencies for IL-2+ cells with CD4+ and CD8+ T cells were correlated with the corresponding frequencies of CCR4 expression in untreated cells using spearman correlation analysis (n=18 points from 6 donors).
Figure 10:
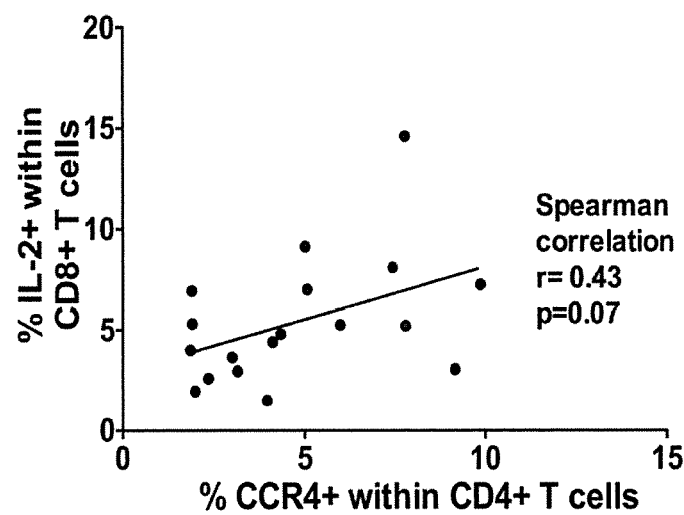

The expression of CCR4 is induced under $T_H2$ polarising conditions. The inventors therefore examined whether CCR4 up-regulation was due to Th2 polarisation by mafosfamide. The expression of IL-4 on PBMCs was correlated with CCR4 expression over a 3-day time course at daily intervals. There were no correlation between CCR4 expression and IL-4 expression in both CD4+ and CD8+ T cell populations (FIG. 9A). Instead, CCR4 expression was positively correlated with the frequency of IL-2+ cells in both CD4+ and CD8+ T cells (FIG. 10).

The inventors further investigated whether mafosfamide induced CCR4 expression on purified CD4+ and CD8+ T cell populations. The fold change in CCR4+ frequency between untreated and mafosfamide treated cells was determined and compared between whole PBMCs and isolated cells. There were no differences in the mean fold increase in frequency of CCR4+ cells within purified CD4+ and purified CD8+ T cells compared to CD4+ and CD8+ T cells contained in whole PBMCs (FIG. 9B).

Figure 11:
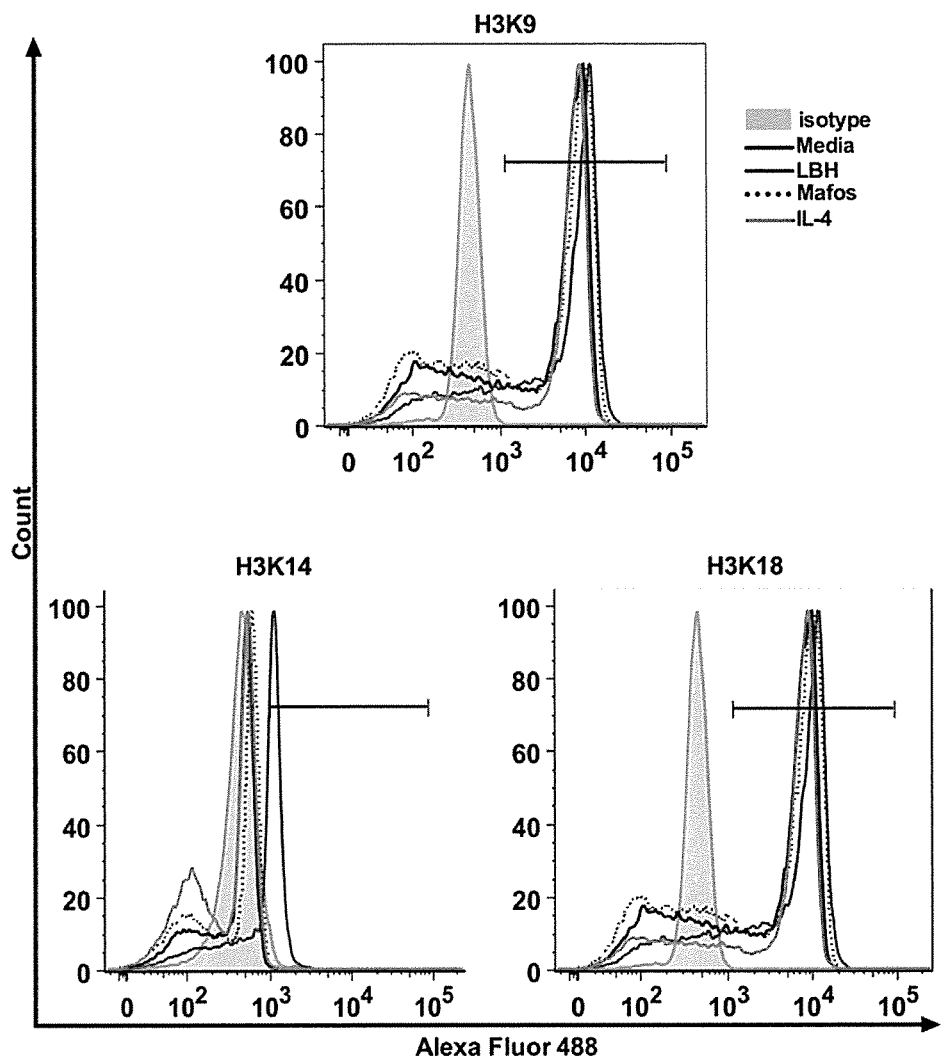
FIG. 11 Representative plots of H3K9, H3K14 and H3K18 acetylation. Healthy donor PBMCs were treated with 1.5 μg/ml of mafosfamide for 72 hours. Acetylation of H3K9, H3K14 and H3K18 was determined using flow cytometry as described in the methods section. Gates for positive cells were set based on the isotype. To compare changes in acetylation levels, the MFI of cells in the positive gate for each treatment group was then normalised to that of media.

Mafosfamide appeared to be directly regulating CCR4 expression. Since cyclophosphamide has previously been shown to act as a histone deacetylase (HDAC) inhibitor, modulating acetylation on histone 3 (H3) and furthermore, since epigenetic modification H3 have been associated with CCR4 gene expression, the inventors investigated whether the control of CCR4 expression by mafosfamide was due to epigenetic modifications. The acetylation levels of H3K9, H3K14 and H3K18 were determined following treatment of PBMCs with panobinostat (LBH589, a pan HDAC inhibitor), mafosfamide or IL-4. The MFI of H3K9, H3K14 or H3K18 positive cells was determined and normalised to that of cells cultured in media alone. Neither mafosfamide nor IL-4 treatment resulted in a change in the acetylation of H3K14 (FIG. 11). Changes in acetylation were evident in H3K9 and H3K18. Gates were set on positive cells and within them the MFIs of acetylated H3K9 and acetylated H3K18 were determined. There was a significant, close to 1.2 fold increase (p<0.05) in the MFI of acetylated H3K9 and H3K18 in both CD4+ and CD8+ T cells when cells were treated with mafosfamide. Treating cells with IL-4 resulted in a slight but significant decrease (p<0.05) in the acetylation of H3K9 in CD8+ T cells (FIG. 9C). There were no significant differences in the acetylation of H3K9 or H3K18 when CCR4+ cells were compared to CCR4− cells within CD4+ and CD8+ T cells (FIG. 9C).

Example 6

Mafosfamide Induced CCR4 Expression Facilitates Cellular Migration Towards CCL22

Figure 12:
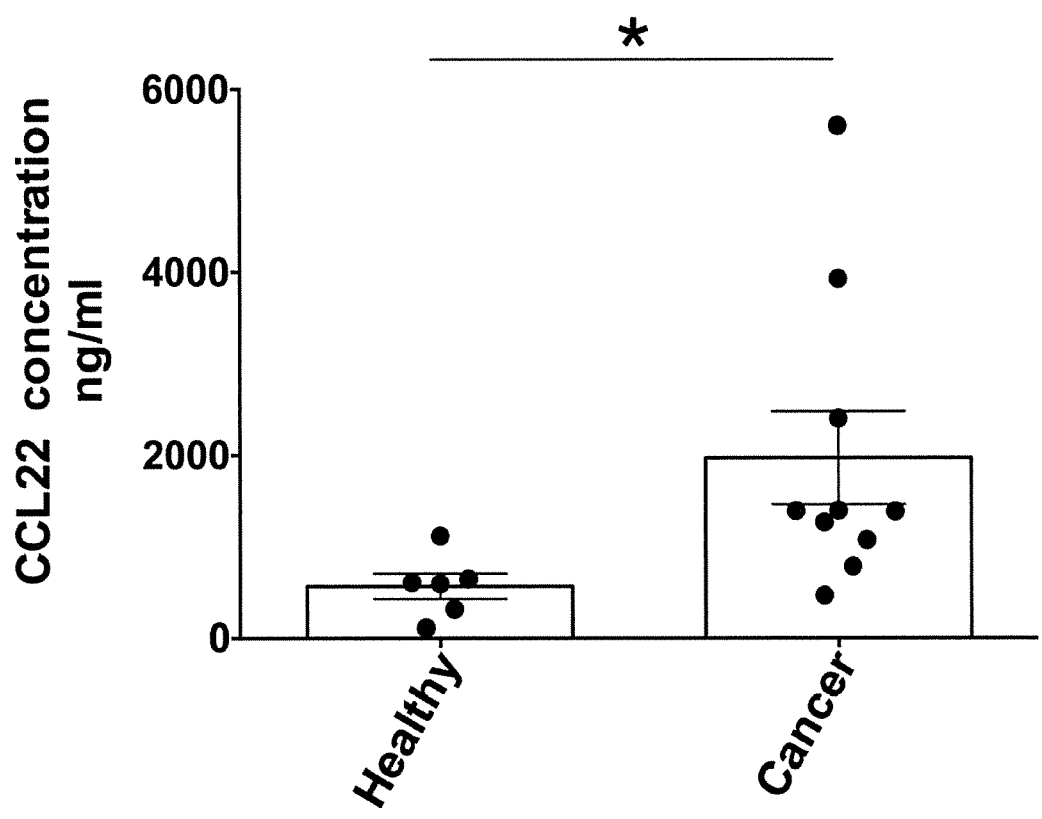
FIG. 12 Mafosfamide induced CCR4 expression allows T cells to migrate towards CCL22. Healthy donor PBMCs were treated with mafosfamide (mafos) as described above. Cells were then seeded into a transwell insert at a concentration of 2.5×105 cells/100 μl and allowed to migrate to the bottom chamber containing either CCL22 (100 ng/ml) or media alone for 2 hours. A the migration index was calculated by dividing the number of cells that migrated towards CCL22 by the number of cells that migrated towards media. The migration indices were plotted for untreated and mafosfamide treated cells (n=7). * represents p<0.05 statistical significance in fold change from untreated levels. B the migration indexes were correlated with the corresponding frequencies of CCR4+ T cells using spearman correlation analysis (n=14 points from 7 donors). C the ratio of Tconvs to Tregs and CD8+ T cell to Tregs that migrated were compared between untreated and Mafosfamide treated cells (n=7 donors). * represents p<0.05 statistical significance between treatment groups. Graphs show means±standard error of the mean (SEM).

To determine whether cyclophosphamide induced CCR4 expression was functional and could initiate cellular migration in response to CCL22, in vitro migration assays were conducted using healthy donor PBMCs treated with 1.5 µg/ml mafosfamide. Migration indices were calculated as previously described (Govindaraj C et al. (2013) Clinical Immunology 149(1):97-110). Serum concentration of CCL22 in patients is shown in FIG. 12.

Figure 13:
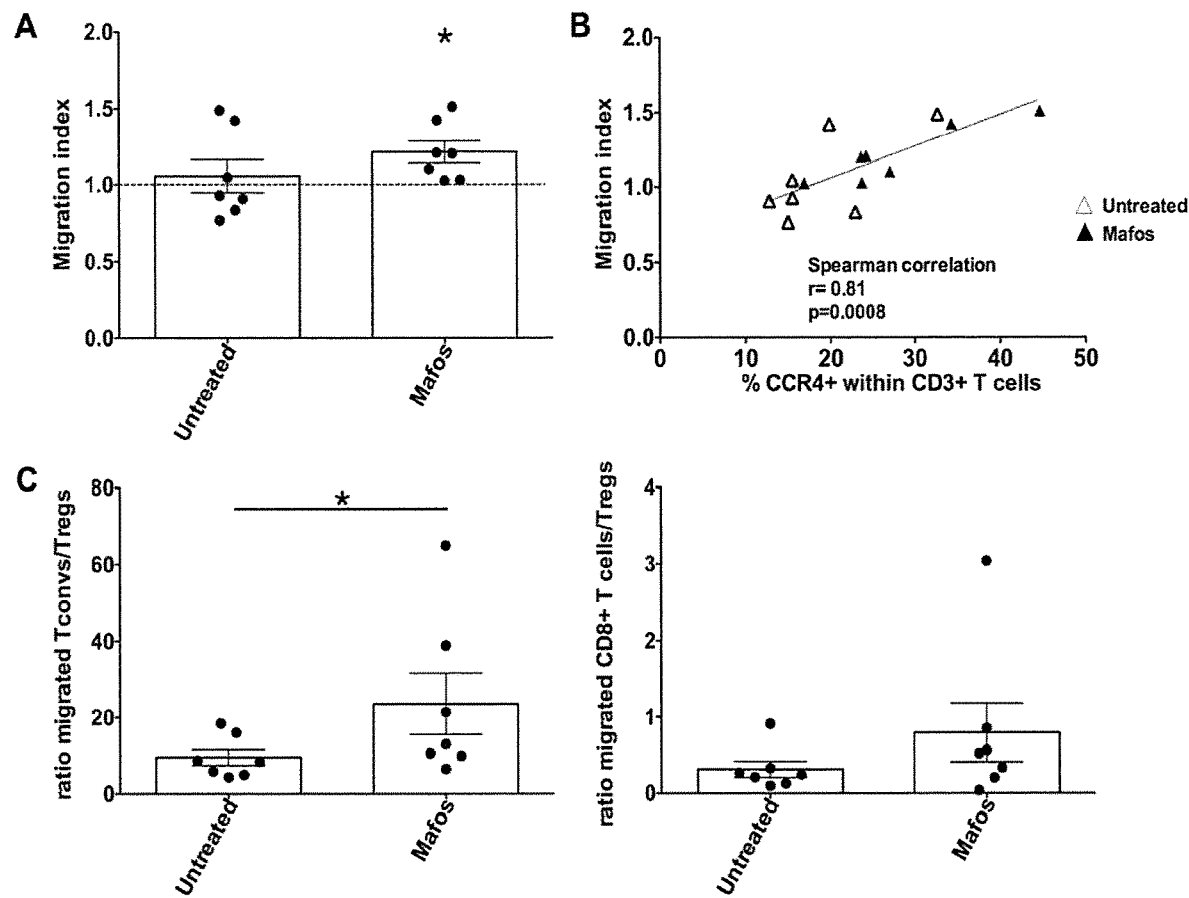
FIG. 13 Serum concentration of CCL22. The concentration of CCL22 in sera from patients pre-treatment (n=10 patients) and from healthy donors (n=5 donors) were determined using a Multiplex Bead Immunoassay Kit. * represents p<0.05 statistical significance between patient and healthy donors. Graphs show means±standard error of the mean (SEM).

There was a significant increase in the migration index of mafosfamide treated PBMCs towards CCL22 (p<0.05), while that of untreated PBMCs remained unchanged (FIG. 13A). To further confirm that this directional migration was related to CCR4 expression, the inventors correlated the frequency of CCR4+ T cells with the migration index and found a significant positive correlation between the two parameters (p<0.001, r=0.81, FIG. 13B).

It is shown that, by differentially up-regulating CCR4 expression on effector cell populations and not on Tregs, cyclophosphamide results in a shift in the ratio of effector cell to Tregs that have potential to migrate to the tumour. The inventors therefore investigated whether this was reflective of an actual shift in the ratio of effector to Tregs within the cells that trafficked towards CCL22. The ratio of Tconvs and CD8+ T cells to Tregs within cells that migrated towards CCL22 was compared between PBMCs that had or had not been treated with mafosfamide. Both mean ratios of Tconvs to Tregs and CD8+ T cells to Tregs were over 2 fold higher in mafosfamide treated cells compared to untreated cells, however this difference was only significant for the ratio of Tconvs to Tregs ($p<0.05$, FIG. 13C).

Example 7

LDCy Increases CCR4$^+$ CD8$^+$ T Cells in Peripheral Blood and Activated CD8 T Cells in TILs in an Immunocompetent Mouse Model of Ovarian Cancer To test the prediction from the pilot human trial in Example 1 that bioactive effector CD8 T cells would be proportionally increased over Treg in tumour infiltrating lymphocytes (TILs) by low dose cyclophosphamide (LDCy) in vivo, the inventors adapted an immunocompetent murine ovarian cancer (OC) model based on a syngeneic epithelial carcinoma cell line ID8, which administered peritoneally (i.p.) or intrabursally (i.b.) recapitulates key aspects of ovarian cancer pathology, including vascular changes, slow growth, formation of tumour ascites and pattern of dissemination (Chiriva-Internati M et al. (2010) PloS one 5, e10471).

Figure 14:
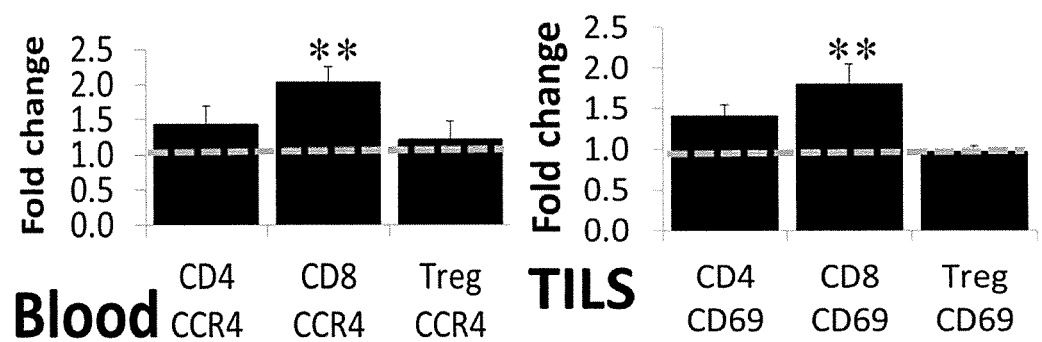
FIG. 14. Increases in CD8 T cells expressing CCR4 in peripheral blood by LDCy 14 days post-treatment in ID8 tumour bearing animals, normalised to control saline treated mice; with concomitant increases in tumour infiltrating lymphocytes (TILS) for activated CD8 T cells expressing CD69 ** represents p<0.02.

To address the effects of LDCy on immunity in tumour bearing animals, ID8 implanted animals (n=5/group) were treated at post challenge (at the onset of detectable tumour growth in vivo) with one cycle of LDCy and assessed changes in T cell subsets ex-vivo at days 1, 7 and 14 post in vivo treatment by flow cytometry. FIG. 14 shows data from day 14. In peripheral blood the inventors found clear increases in CCR4$^+$CD8$^+$ T cells apparent (FIG. 14A), a trend towards CCR4$^+$ CD4 T cell effector increases, and similarly to the human trial results, no increases in CCR4$^+$ Treg. Since CCR4 is down-regulated by CCL22 secreted locally by the tumour (Mariani M et al., (2004) Eur J Immunol 34:231; de Lavareille A et al (2001) European Journal of Immunology 31:1037-1046), and CCR4 mediated T cell infiltration is associated with an activated phenotype (Kovacsovics-Bankowski M et al., (2014) Journal for immunotherapy of cancer 2:38), the inventors also tested for concomitant changes in the frequency of activated T cells in tumour infiltrating lymphocytes (TILS) by co-staining with the CD69 activation marker. FIG. 14B shows TILS CD69+ CD8+ T cells clearly increased post LDCy treatment, with again a trend towards CD69$^+$ CD4 T cell effector increases, but no CD69$^+$Treg increases further correlated to CCR4$^+$ T cell increases in blood (not shown).

Example 8

Predicting Responders to Cyclophosphamide Treatment

Peripheral blood mononuclear cells (PBMC) are obtained from a cancer subject and isolated via Ficoll density gradient centrifugation within 24 hours of blood collection. The cells are then suspended in AMI-V medium with 5% human serum. The PBMCs are then cultured for 3 days with 1.5 µg/ml of mafosfamide or media alone under appropriate conditions for 3 days. The cells are then harvested and stained with appropriate cell surface markers including CCR4, CD3, CD8, CD4, and CD25 and a fixable dead cell dye (e.g. PE) to distinguish dead cells. Intracellular levels of FoxP3 are determined following fixation and permeabilisation of the cells followed by labelling with anti-FoxP3. The cells are then appropriately gated and analysed by flow cytometry by reference to isotype-matched controls. Teff cells expressing FoxP3−, CD25−, CD4+ and CD8+ are analysed for expression of CCR4. In some cases, Tregs expressing FoxP3+, CD25+, CD4+ are also analysed for expression of CCR4.

The level of CCR4 expression on Teff cells cultured in the presence of mafosfamide is compared to the level of level of CCR4 expression on cells cultured in the absence of mafosfamide.

Subjects who demonstrate an increase in CCR4 expression (i.e. upregulation) following mafosfamide treatment compared to the untreated cells are selected for treatment with low-dose cyclophosphamide or an analogue, derivate or active metabolite thereof.

Remarks

The emphasis of immunotherapy for cancer has been on ameliorating immunosuppression and activating effector T cell function (Dougan M and Dranoff G (2009) Ann Rev Immunol. 27:83-117). However, these efforts are futile if beneficial immune cells cannot get to where they are needed. The data presented herein indicates that it is possible to pre-identify patients who will respond immunologically and benefit from immunotherapeutic low dose cyclophosphamide (LDCy) treatment using an in vitro screening protocol. The screening test may be combined with genetic tests to provide additional power.

The effects of LDCy on CCR4 upregulation were consistent on effector T cells, but not Tregs with a dramatic increase in survival (>300 days) for patients observed to have CCR4 up-regulation in vivo during treatment and in vitro in the CUP pre-test.

Animal data supported the hypothesis that LDCy increases effector CCR4+ CD8+ T cells in blood (but not CCR4+ T reg) promoting their subsequent migration tumours, enriching the tumour infiltrate in activated CD8 T cells. Importantly, the pre-treatment in vitro analysis of human PBMC would also predict patient who would not respond to LDCy treatment, enabling them to move on to other treatments.

These data suggest that cyclophosphamide is capable of directly switching on the expression of CCR4 in effector T cells. The migration assay confirmed the ability of mafosfamide treated cells to migrate in response to CCL22 and also showed that there was an increase in the ration of effector T cells to Tregs in the migrated fraction.

The invention claimed is:

1. A method for treating a cancer subject who will clinically respond to treatment with cyclophosamide or an analogue thereof, the method comprising:

(a) identifying a cancer subject who will clinically respond to treatment with cyclophosamide or an analogue thereof by:
(i) obtaining a biological sample from the subject comprising Teff cells;

(ii) detecting expression of CCR4 on the Teff cells in the biological sample by contacting the Teff cells in the sample with an agent that binds to CCR4 on the surface of Teff cells, and measuring the level of expression of CCR4 on the cells;

(iii) administering to the subject at least one low dose or low dose cycle of cyclophosphamide or an analogue thereof;

(iv) detecting expression of CCR4 on Teff cells in a biological sample obtained from the subject after administration;

(v) comparing the level of expression of CCR4 on the Teff cells in (iv) with the level of expression of CCR4 on Teff cells in (ii);

wherein upregulation of CCR4 expression on the Teff cells after administering indicates that the subject will clinically respond to further in vivo treatment with low dose cyclophosphamide or an analogue thereof;

wherein the Teff cells comprise CD3+CD8+ cells and/or CD3+FoxP3−CD25−CD4+ cells; and (b) treating the subject who will clinically respond with low dose cyclophosphamide or an analogue thereof.

2. The method according to claim 1, wherein the subject has a gynaecological cancer.

3. The method according to claim 1, wherein the biological sample from the subject further comprises Tsupp cells; and wherein step (ii) further comprises detecting expression of CCR4 on the Tsupp cells in the biological sample by contacting the Tsupp cells in the sample with an agent that binds to CCR4 on the surface of Tsupp cells and measuring the level of expression of CCR4 on the Tsupp cells; and step (iv) further comprises detecting expression of CCR4 on the Tsupp cells in a biological sample obtained from the subject after administration;

wherein upregulation of CCR4 expression on the Teff cells but not the Tsupp cells after administering is indicative that the subject will clinically respond to further in vivo treatment with cyclophosphamide or an analogue thereof;

wherein the Tsupp cells comprise CD3+FoxP3+CD25+CD4+ cells.

4. The method according to claim 1, wherein the biological sample comprises peripheral blood mononuclear cells (PBMCs).

5. The method according to claim 1, wherein the Teff cells comprise CD4+ TH1 T cells and/or CD8+ cytotoxic T cells.

6. The method of claim 1, wherein the CD8+ cells are also CD69+.

7. The method of claim 2, wherein the gynaecological cancer is ovarian cancer.

8. A method for treating a cancer subject who has not previously received cyclophosphamide or an analogue thereof, and who will clinically respond to treatment with cyclophosphamide or an analogue thereof, the method comprising:

(a) predicting that the subject will respond to treatment with cyclophosphamide or an analogue thereof by:

(i) obtaining a biological sample from the subject comprising Teff cells;

(ii) detecting expression of CCR4 on the Teff cells in the biological sample by contacting the Teff cells in the sample with an agent that binds to CCR4 on the surface of Teff cells and measuring the level of expression of CCR4 on the cells;

(iii) exposing the biological sample to cyclophosphamide or an analogue thereof in vitro;

(iv) detecting expression of CCR4 on the Teff cells by contacting the Teff cells in the biological sample from the subject with an agent that binds to CCR4 on the surface of Teff cells; and measuring the level of expression of CCR4 on the cells, (v) comparing the level of expression of CCR4 on the Teff cells in (iv) with the level of expression of CCR4 on Teff cells in (ii);

wherein upregulation of CCR4 expression on Teff cells following the exposure indicates that the subject will clinically respond to further in vivo treatment with cyclophosphamide or an analogue thereof, wherein the Teff cells comprise CD3+CD8+ cells and/or CD3+FoxP3−CD25−CD4+ cells; and (b) treating the subject predicted to clinically respond with low dose cyclophosphamide or an analogue thereof.

9. The method according to claim 8, wherein the subject has a gynaecological cancer.

10. The method according to claim 8, wherein the biological sample from the subject further comprises Tsupp cells; and wherein:

step (ii) further comprises detecting expression of CCR4 on the Tsupp cells in the biological sample by contacting the Tsupp cells in the sample with an agent that binds to CCR4 on the surface of Tsupp cells and measuring the level of expression of CCR4 on the Tsupp cells; and step (iv) further comprises detecting expression of CCR4 on the Tsupp cells in the biological sample obtained from the subject;

wherein upregulation of CCR4 expression on the Teff cells but not the Tsupp cells following the exposure indicates that the subject will clinically respond to treatment with cyclophosphamide or an analogue thereof, wherein the Tsupp cells comprise CD3+FoxP3+CD25+CD4+ cells.

11. The method according to claim 8, wherein the cells are exposed to mafosfamide in vitro for 3 days.

12. The method according to claim 8, wherein the method comprises comparing the level of CCR4 expression determined in step (iv) with the level of CCR4 expression on Teff cells from control subjects.

13. The method according to claim 8, wherein the biological sample comprises peripheral blood mononuclear cells (PBMCs).

14. The method of claim 8, wherein the Teff cells comprise CD3+FoxP3−CD25−CD4+ cells.

15. A method for treating a subject with a gynaecological cancer, comprising:

(A) determining whether the subject will be clinically responsive to low dose treatment with cyclophosphamide or an analogue thereof, by:

(i) obtaining a biological sample from the subject comprising Teff cells;

(ii) detecting expression of CCR4 on the Teff cells in the biological sample by contacting the Teff cells in the sample with an agent that binds to CCR4 on the surface of Teff cells and measuring the level of expression of CCR4 on the cells;

(iii) administering to the subject at least one low dose or low dose cycle of cyclophosphamide or an analogue thereof;

(iv) detecting expression of CCR4 on the Teff cells in a biological sample obtained from the subject after administration;

(v) comparing the level of expression of CCR4 on the Teff cells in (iv) with the level of expression of CCR4 on the Teff cells in (ii);

wherein upregulation of CCR4 expression on the Teff cells after administering indicates that the subject will clinically respond to further in vivo treatment with low dose cyclophosphamide or an analogue thereof, and lack of upregulation of CCR4 expression on the Teff cells after administering indicates that the subject will not clinically respond to in vivo treatment with low dose cyclophosphamide or an analogue thereof;

wherein the Teff cells comprise CD3+CD8+ cells and/or CD3+FoxP3−CD25−CD4+ cells; and (B) treating the subject with an anti-cancer treatment, wherein:

(i) if the subject is determined to be clinically responsive to further in vivo treatment with low dose cyclophosphamide or an analogue thereof, the treatment comprises administration of low dose cyclophosphamide or an analogue thereof; and (ii) if the subject is determined to be not clinically responsive to further in vivo treatment with low dose cyclophosphamide or an analogue thereof, the treatment comprises an alternative anti-cancer treatment that does not comprise administration of cyclophosphamide or an analogue thereof.

16. The method of claim 15, wherein the gynaecological cancer is ovarian cancer.

17. The method according to claim 15, wherein the biological sample from the subject further comprises Tsupp cells; and wherein step (ii) further comprises detecting expression of CCR4 on the Tsupp cells in the biological sample by contacting the Tsupp cells in the sample with an agent that binds to CCR4 on the surface of Tsupp cells and measuring the level of expression of CCR4 on the Tsupp cells; and step (iv) further comprises detecting expression of CCR4 on the Tsupp cells in a biological sample obtained from the subject after administration;

wherein upregulation of CCR4 expression on the Teff cells but not the Tsupp cells after administering is indicative that the subject will clinically respond to further in vivo treatment with cyclophosphamide or an analogue thereof;

wherein the Tsupp cells comprise CD3+FoxP3+CD25+CD4+ cells.

18. The method according to claim 15 wherein the method comprises comparing the level of CCR4 expression determined in step (iv) with the a level of CCR4 expression on Teff cells from control subjects.

19. The method according to claim 15, wherein the biological sample comprises peripheral blood mononuclear cells (PBMCs).

20. The method according to claim 15, wherein the Teff cells comprise CD4+ TH1 T cells and/or CD8+ cytotoxic T cells.

21. The method of claim 15, wherein the CD8+ cells are also CD69+.

* * * * *